United States Patent [19]

Sirrenberg et al.

[11] B 4,013,795

[45] Mar. 22, 1977

[54] COMBATING PESTS WITH DICHLOROVINYLTHIONOPHOSPHORIC ACID ESTER AMIDES

[75] Inventors: Wilhelm Sirrenberg, Sprockhovel im westphalia; Bernhard Homeyer, Opladen; Ingeborg Hammann, Cologne; Wilhelm Stendel, Wuppertal-Elberfeld, all of Germany

[73] Assignee: Bayer Aktiengesellschaft, Leverkusen, Germany

[22] Filed: Sept. 30, 1974

[21] Appl. No.: 510,836

[44] Published under the second Trial Voluntary Protest Program on March 23, 1976 as document No. B 510,836.

Related U.S. Application Data

[63] Continuation-in-part of Ser. No. 267,759, June 30, 1972, abandoned.

[30] Foreign Application Priority Data

July 3, 1971    Germany ........................ 2133200

[52] U.S. Cl. ..................... 424/219; 260/940; 260/950; 260/957; 424/210
[51] Int. Cl.² .......................................... A01N 9/36
[58] Field of Search .......... 424/219, 210; 260/950, 260/957

[56] References Cited

UNITED STATES PATENTS 2,861,912   11/1958   Sallmann ................. 260/957 X
3,264,184   8/1966   Geiger et al. .............. 260/957 X
3,632,692   1/1972   Morales .................... 260/957 X
3,652,742   3/1972   Sirrenberg et al. ......... 260/957
3,745,198   7/1973   Soloway et al. ............ 260/957

Primary Examiner—Leonard Schenkman
Attorney, Agent, or Firm—Burgess, Dinklage & Sprung

[57] ABSTRACT

Dichlorovinylthionophosphoric acid ester amides of the formula

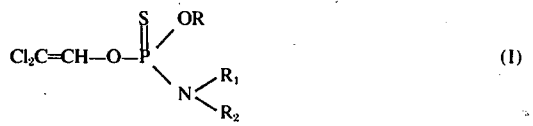

in which
R is alkyl of 1 to 16 carbon atoms which may be substituted by alkoxy of 1 to 6 carbon atoms, cycloalkyl, cycloalkenyl, cyano, halo or aryl; cycloalkyl; aryl; or alkylaryl, and
$R_1$ and $R_2$ each independently is hydrogen; alkyl of 1 to 8 carbon atoms which may be substituted by aryl, cyano or alkoxy; aryl; or alkenyl of 2 to 8 carbon atoms; or together with the nitrogen atom to which they are attached form a heterocyclic ring,
which possess insecticidal, acaricidal, nematocidal, rodenticidal, fungicidal and bactericidal properties.

8 Claims, No Drawings

COMBATING PESTS WITH DICHLOROVINYLTHIONOPHOSPHORIC ACID ESTER AMIDES

This application is a continuation-in-part of application Ser. No. 267,759, filed June 30, 1972, now abandoned.

The present invention relates to and has for its objects the provision of particular new dichlorovinylthionophosphoric acid ester amides i.e. O-(optionally substituted-alkyl-, -aryl- or -cycloalkyl)-N-(unsubstituted-, mono- or disubstituted)-dichlorovinylthionophosphoric acid ester amides, which possess insecticidal, acaricidal, nematocidal, rodenticidal, fungicidal and bactericidal properties, active compositions in the form of mixtures of such compounds with solid and liquid dispersible carrier vehicles, and methods for producing such compounds and for using such compounds in a new way especially for combating pests, e.g. insects, acarids, nematodes, rodents, fungi and bacteria, especially insects, acarids and nematodes, with other and further objects becoming apparent from a study of the within specification and accompanying examples.

It is already known from German Published Specification (DAS) 1,083,253 that O,O-dialkyl-O-[2,2-dichlorovinyl]-phosphoric acid esters, for example O,O-dimethyl-O-[2,2-dichlorovinyl]-phosphoric acid ester, (Compound A) possess an insecticidal action.

The present invention provides, as new compounds, the dichlorovinylthionophosphoric acid ester amides of the formula

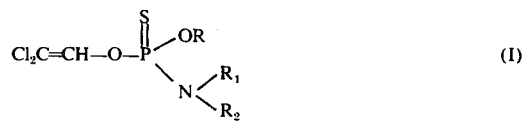

in which
R is alkyl of 1 to 16 carbon atoms which may be substituted by alkoxy of 1 to 6 carbon atoms, cycloalkyl, cycloalkenyl, cyano, halo or aryl; cycloalkyl; aryl; or alkylaryl, and
$R_1$ and $R_2$ each independently is hydrogen; alkyl of 1 to 8 carbon atoms which may be substituted by aryl, cyano or alkoxy; aryl; or alkenyl of 2 to 8 carbon atoms; or together with the nitrogen atom to which they are attached form a heterocyclic ring.

Surprisingly, the dichlorovinylthionophosphoric acid ester amides according to the invention are distinguished by a considerably better insecticidal, especially soil-insecticidal, acaricidal and nematocidal action than the known O,O-dialkyl-O-[2,2-dichlorovinyl]-phosphoric acid esters of analogous structure and identical type of action. The compounds according to the invention hence represent a genuine enrichment of the art.

Preferably, in formula (I) above, R is alkyl with 1 to 12 carbon atoms (for example methyl, ethyl, n- or isopropyl, n-, sec-, tert.- or isobutyl, n-, iso- or neopentyl, n-hexyl, n-heptyl, n-octyl, 2-ethylbutyl, 2,2-dimethylbutyl, 2-ethylhexyl, 2,2-dimethylhexyl, n-decyl, 2,2-dimethyloctyl, n-dodecyl or 2,2-dimethyldecyl), 2,2,2-trichloroethyl, 1,3-dichloropropyl, 2-chloroethyl, 2-bromoethyl, cyanoethyl, cyclopentyl, cyclohexyl, cyclopentylmethyl, cyclopentylethyl, cyclopentylpropyl, cyclohexylmethyl, cyclohexylethyl, cyclohexylpropyl, cyclohexen-3-yl-methyl, phenyl, alkylphenyl (for example 4-methyl-,4-ethyl-, 4-n- or isopropyl- or 4-tert.-butylphenyl), benzyl, phenethyl, 3-phenylpropyl, methoxymethyl, methoxyethyl, methoxypropyl, methoxybutyl, ethoxymethyl, ethoxyethyl, ethoxypropyl, ethoxybutyl, propoxymethyl, propoxyethyl, propoxypropyl, butoxyethyl or butoxypropyl; and $R_1$ and $R_2$ are individually hydrogen, cyanoethyl, benzyl, phenethyl, lower alkyl with 1 to 4 carbon atoms alkoxyalkyl with 1 to 4 carbon atoms per alkyl moiety or lower alkenyl with 3 or 4 carbon atoms (for example propenyl, allyl, buten-1-yl, buten-2-yl or isobutenyl) or, conjointly with the nitrogen atom, form a morpholino, pyrrolidine or piperidine radical.

A preferred sub-group of compounds is those wherein $R_1$ is hydrogen, R is methyl, isopropyl, isobutyl or sec.-butyl and $R_2$ is methyl, ethyl, propyl or allyl. Of these, especially preferred are
O-isobutyl-O-(2,2-dichlorovinyl)-N-methyl-thionophosphoric acid ester amide,
O-methyl-O-(2,2-dichlorovinyl)-N-allyl-thionophosphoric acid ester amide,
O-methyl-O-(2,2-dichlorovinyl)-N-propyl-thionophosphoric acid ester amide,
O-isopropyl-O-(2,2-dichlorovinyl)-N-ethyl-thionophosphoric acid ester amide, and
O-isobutyl-O-(2,2-dichlorovinyl)-N-ethyl-thionophosphoric acid ester amide.

The present invention also provides a process for the preparation of a dichlorovinylthionophosphoric acid ester amide of the formula (I) in which dichlorovinylthionophosphoric acid ester dichloride of the formula

is reacted with a hydroxy compound of the general formula

ROH     (III)

in which
R has the meaning stated above,
in the presence of an acid-binding agent to give the corresponding monochloride, which is subsequently reacted, optionally without prior isolation, with an amino compound of the general formula

in which
$R_1$ and $R_2$ have the meaning stated above,
also in the presence of an acid-binding agent.

If O-[2,2-dichlorovinyl]-thionophosphoric acid ester dichloride, ethanol and dimethylamine are used as the starting materials, the course of the reaction can be represented by the following equation:

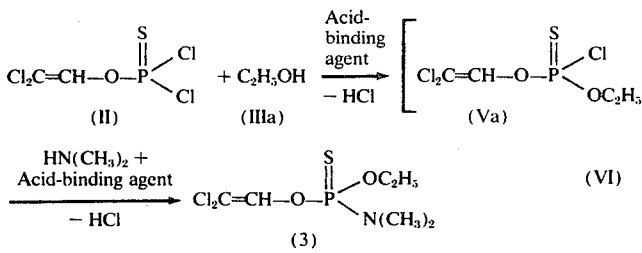

As examples of the primary and secondary amines and hydroxy compounds that can be employed in the preparative process, the following compounds may be mentioned: methylamine, ethylamine, n- or isopropylamine, n-, sec.-, tert.- or isobutylamine, 2-cyanoethylamine, benzylamine, phenethylamine allylamine, propenylamine, buten-1-ylamine, buten-2-ylamine or isobutenylamine, also dimethylamine, diethylamine, di-isopropylamine, dipropylamine, di-isobutylamine, di-n-butylamine or di-tert.-butylamine, as well as morpholine, pyrolidine or piperidine, and also methyl, ethyl, n- and isopropyl, n-, sec.-, tert.- or isobutyl, n-, iso- or neopentyl, n-hexyl, n-heptyl, n-octyl, 2-ethylbutyl, 2,2-dimethylbutyl, 2-ethylhexyl, 2,2-dimethylhexyl, n-decyl, 2,2-dimethyloctyl, n-dodecyl, 2,2-dimethyldecyl,2,2,2-trichloroethyl, 1,3-dichloropropyl, 2-chloroethyl, 2-cyanoethyl, cyclopentyl, cyclohexyl, cyclopentylmethyl, cyclopentylethyl, cyclopentylpropyl, cyclohexylmethyl, cyclohexylethyl, cyclohexylpropyl, cyclohexen-3-yl-methyl, benzyl, phenethyl, 3-phenylpropyl, methoxymethyl, methoxyethyl, methoxypropyl, methoxybutyl, ethoxymethyl, ethoxyethyl, ethoxypropyl, ethoxybutyl, propoxymethyl, propoxyethyl, propoxypropyl, butoxyethyl or butoxypropyl alcohol, as well as phenol and p-methylmercaptophenol.

The hydroxy and amino compounds required as the starting materials are known from the literature and are also easily obtainable on an industrial scale. O-[2,2-dichlorovinyl]-thionophosphoric acid ester dichloride can be obtained, in accordance with a process that does not form part of the state of the art, from O-[2,2-dichlorovinyl]-phosphoric acid ester dichloride, phosphorus pentasulfide and phosphorus sulfochloride at temperatures between 110° and 160°C in the presence of a solvent.

The preparative process for the compounds of this invention is preferably carried out with the use of a suitable solvent or diluent. Practically all inert organic solvents can be used for this purpose; especially suitable are aliphatic and aromatic hydrocarbons (which may be chlorinated), such as benzene, toluene, xylene, petroleum ether, benzine, methylene chloride, chloroform, carbon tetrachloride or chlorobenzene, ethers, for example diethyl ether, dibutyl ether or dioxane, ketones, for example acetone, methyl ethyl ketone, methyl isopropyl ketone or methyl isobutyl ketone, and nitriles, such as acetonitrile or propionitrile.

As an acid-binding agent it is possible to use any customary acid acceptor. Alkali carbonates and alkali alcoholates, such as sodium and potassium carbonate, sodium and potassium methylate and sodium and potassium ethylate, as well as aliphatic, aromatic and heterocyclic amines, for example triethylamine, dimethylamine, dimethylaniline, dimethylbenzylamine and pyridine, have proved particularly successful.

The reaction temperature can be varied within a fairly wide range. In general, the reaction is carried out at about 0° to 100°C, preferably at about 20° to 50°C. The reaction is generally effected at normal pressure.

Generally, to carry out the process, the reaction of the O-[2,2-dichlorovinyl]-thionophosphoric acid ester dichloride is effected by dissolving the latter in a suitable solvent or diluent and first adding to this solution, while stirring and at the indicated temperatures, an appropriately cooled mixture of the particular hydroxy compound, acid-binding agent and solvent. Thereafter, the salt-like precipitate that has separated out is filtered off and eluted with the solvent employed. The filtrate is treated dropwise with a mixture of the amino compound, solvent and acid-binding agent, though it is also possible to choose the converse sequence, and thereafter the reaction mixture is stirred for some time longer at room temperature. The reaction mixture is worked up in a manner which is in itself known, by filtering off the salt that has separated out, washing and neutralizing the filtrate and drying it, evaporating the solvent, preferably under reduced pressure, and, if appropriate, fractionally distilling the residue.

It is, however, also possible, after adding the particular hydroxy compound, not to separate off the salt-like precipitate that has separated out but to add a mixture of the amine, solvent, and acid-binding agent after a certain time. The reaction mixture is then worked up as described above.

The substances according to the invention are in most cases obtained in the form of colorless to pale yellow-colored oils which sometimes cannot be distilled without decomposition, but can however be freed of the last volatile constituents, and thus purified, by so-called "slight distillation," that is to say by prolonged heating under reduced pressure and at moderately elevated temperature. The substances are characterized, for example, by the refractive index. If the NMR-spectrum, the chromatogram or the elementary analysis shows that non-volatile impurities are contained in the product which has been subjected to "slight distillation," a separation from the impurities can frequently be achieved by extracting the product with nonpolar solvents, for example petroleum ether.

As has already been mentioned, the new dichlorovinylthionophosphoric acid ester amides are distinguished by an outstanding insecticidal, above all soil-insecticidal, acaricidal and nematocidal activity towards plant pests, pests harmful to health and storage pests, and towards ectoparasites. At the same time they possess a good action both against sucking and against biting insects and mites (Acarina). Above all, they are also active against those acarids which as animal ectoparasites attack domesticated animals. Furthermore, their good action against parasitary fly larvae should be mentioned. At the same time they show a low phytotoxicity and, in some cases, also rodenticidal, fungicidal and bactericidal properties. The compounds according to the invention may therefore be employed as pesticides, particularly in plant protection and the protection of stored products, and also in the hygiene and veterinary fields.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzur cerasi*); in addition, scales and mealybugs (Coccina), for example the oleander scale (*Aspidiotus hederae*) and the soft scale (*Lecanium hesperidum*)as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly caterpillars (Lepidoptera) such as the diamond-back moth (*Plutella maculipennis*), the gipsy moth (*Lymantria dispar*), the browntail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma fragiperda*) and cotton worm (*Prodenia litura*), the ermine moth (*Hyponomeuta padella*), the Mediterranean flour moth (*Ephestia kuhniella*) and greater wax moth (*Galleria mellonella*).

Also to be classed with the biting insects are beetles (Coleoptera), for example the granary weevil (*Sitophilus granarius = Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius = A canthoscelides obtectus*), the leather beetle (*Dermestes frischi*), the khapra beetle (*Trogoderma granarium*), the flour beetle (*Tribolium castaneum*), the northern corn billbug (*Calandra* or *Sitophilus zeamais*), the drugstore beetle (*Stegobium paniceum*), the yellow mealworm (*Tenebrio molitor*) and the saw-toothed grain bettle (*Oryzaephilus surinamensis*), but also species living in the soil, for example wireworms (*Agriotes spec.*) and larvae of the cockchafer (*Melolontha melolontha*); cockroaches, such as the German cockroach (*Blattella germanica*), American cockroach (*Periplaneta americana*), Madeira cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Acheta domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (Acarina) there are classed, in particular, the spider mites (Tetranychidae) such as the twospotted spider mite (*Tetranychus urticae*) and the European red mite (*Paratetranychus pilosus = Panonychus ulmi*), gall mites, for example the black currant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against pests harmful to health and pests of stored products, particularly flies and mosquitoes, the compounds of this invention are also distinguished by an outstanding residual activity on wood and clay, as well as good stability to alkali on limed substrates.

The active compounds according to the instant invention can be utilized, if desired, in the form of the usual formulations or compositions with conventional inert (i.e., plant compatible or herbicidally inert) pesticide diluents or extenders, i.e., diluents, carriers or extenders of the type usable in conventional pesticide formulations or compositions, e.g., conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticides dispersible liquid diluent carriers and/or dispersible solid carriers optionally with the use of carrier vehicle assistants, e.g., conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose; aerosol propellants which are gaseous at normal temperatures and pressures, such as Freon; inert dispersible liquid diluent carriers, including inert organic solvents, such as aromatic hydrocarbons (e.g., benzene, toluene, xylene, alkyl naphthalenes, etc.), halogenated, especially chlorinated, aromatic hydrocarbons (e.g., chlorobenzens, etc.), cycloalkanes (e.g., cyclohexane, etc.), paraffins (e.g., petroleum or mineral oil fractions), chlorinated aliphatic hydrocarbons (e.g., methylene chloride, chloroethylenes, etc.), alcohols (e.g., methanol, ethanol, propanol, butanol, glycol, etc.) as well as ethers and esters thereof (e.g., glycol monomethyl ether, etc.), amines (e.g., ethanolamine, etc.), amides (e.g., dimethyl formamide, etc.), sulfoxides (e.g., dimethyl sulfoxide, etc.), acetonitrile, ketones (e.g., acetone, methyl ethyl ketone, methyl isobutyl ketone, cyclohexanone, etc.), and/or water; as well as inert dispersible finely divided solid carriers, such as ground natural minerals (e.g., kaolins, clays, alumina, silica, chalk, i.e., calcium carbonate, talc, attapulgite, montmorillonite, kieselguhr, etc.) and ground synthetic minerals (e.g., highly dispersed silicic acid, silicates, e.g., alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other acaricides, insecticides, fungicides, bactericides, nematocides and rodenticides, or herbicides, fertilizers, growth-regulating agents, etc., if desired or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprises mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g., a surface-active agent, such as an emulsifying agent and/or a dispersing agent, and an amount of the active compound which is effected for the purpose in question and which is generally between about 0.0001–95%, and preferably 0.01–95%, by weight of the mixture.

The active compounds can also be used in accordance with the well known ultra-low-volume process with good success, i.e., by applying such compound if normally a liquid, or by applying a liquid composition containing the same, via very effective atomizing equipment, in finely divided form, e.g., average particle diameter of from 50–100 microns, or even less, i.e., mist form, for example by airplane crop spraying techniques. Only up to at most about a few liters/hectare are needed, and often amounts only up to about 15 to 1,000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects, acarids, nematodes, rodents, fungi and bacteria and more particularly methods of combating at least one of insects, acarids and nematodes, which comprises applying to at least one of correspondingly (a) such insects, (b) such acarids, (c) such nematodes, (d) such rodents, (e) such fungi, (f) such bacteria, and (g) the corresponding habitat thereof, i.e., the locus to be protected, a correspondingly combative or toxic amount, i.e., an insecticidally, acaricidally, nematocidally, rodenticidally, fungicidally or bacteri-cidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The following examples are set forth to illustrate, without limitation, the process for producing the active compounds according to the present invention.

EXAMPLE 1 a. The O-(2,2-dichlorovinyl)-thionophosphoric acid ester dichloride required as the starting material can, for example, be prepared as follows:

(II)

33 g of phosphorus(V) sulfide are added to 115 g of O-(2,2-dichlorovinyl)-phosphoric acid ester dichloride in 170 g of phosphorus sulfochloride and the mixture is heated to the boil under reflux. When the phosphorus(V) sulfide has dissolved (0.5 to 1.5 hours), the batch is cooled and the solution is decanted from the insoluble matter. The phosphorus sulfochloride is distilled off and the residue is distilled through a column. 84 g (68.3% of theory) of the desired O-(2,2-dichlorovinyl)-thionophosphoric acid ester dichloride of boiling point 75°C/3 mm Hg and refractive index $n_D^{20}$ of 1.5490 are thus obtained.

b.

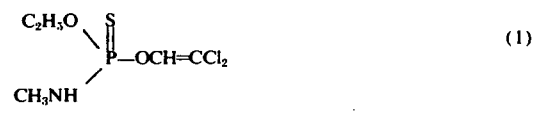

(1)

12.5 g of absolute ethanol and 26 g of triethylamine, dissolved in 100 ml of benzene, are added dropwise, at 5° to 10°C, to a solution of 61.5 g (0.25 mole) of O-(2,2-dichlorovinyl)-thionophosphoric acid ester dichloride in 300 ml of benzene. After completion of the dropwise addition, the batch is stirred for 1.5 hours at 40°C and then cooled to 10°C. Methylamine is passed into the cold solution until it reacts alkaline, and the batch is stirred for a further half-hour at 10°C and a further hour at 30° to 40°C. Thereafter, the salt which has precipitated is filtered off, the filtrate is concentrated under reduced pressure, the oily residue which remains is taken up in methylene chloride, and the methylene chloride solution is washed with water and dried. After distilling off the solvent, an oil remains, which can be distilled without decomposition. 47 g (75% of theory) of the desired O-ethyl-O-(2,2-dichlorovinyl)-N-methyl-thionophosphoric acid ester amide of boiling point 128°–138°C/6 mm Hg and a refractive index $n_D^{20}$ of 1.5111 are obtained.

---

Calculated for $C_5H_{10}Cl_2NO_2PS$ (molecular weight 250.04)

-continued

|        | Cl      | N      | P       | S       |
|--------|---------|--------|---------|---------|
|        | 28.4 %; | 5.6 %; | 12.4 %; | 12.8 %  |
| Found: | 28.5 %; | 5.8 %; | 12.7 %  | 12.6 %. |

EXAMPLE 2

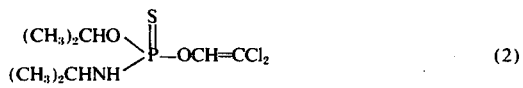

(2)

20.5 g of isopropanol and 34 g of triethylamine, dissolved in 100 ml of benzene, are added dropwise to a solution, cooled to 5°–10°C, of 82 g (0.33 mole) of O-(2,2-dichlorovinyl)-thionophosphoric acid ester dichloride in 300 ml of benzene. The batch is stirred for 1 hour at 40°C and is then cooled to 20°C. At this temperature, a solution of 21 g of isopropylamine and 34 g of triethylamine in 100 ml of benzene is added dropwise to the reaction mixture and the latter is stirred for 2 hours at 40°C. Thereafter the salt which has separated out is filtered off, the filtrate is concentrated under reduced pressure, the oil which remains is taken up in methylene chloride and the methylene chloride solution is washed until it reacts neutral, and dried. After stripping off the solvent, an oil is obtained, which is distilled in order to purify it. 62 g (63.5% of theory) of O-isopropyl-O-(2,2-dichlorovinyl)-N-isopropyl-thionophosphoric acid ester amide of boiling point 102°C/0.001 mm Hg and a refractive index $n_D^{20}$ of 1.5118 are obtained.

Calculated for $C_8H_{16}Cl_2NO_2PS$ (molecular weight 292.17)

|        | Cl      | N      | P       | S       |
|--------|---------|--------|---------|---------|
|        | 23.27 %;| 4.79 % | 10.60 %;| 10.97 % |
| Found: | 24.90 %;| 4.72 %;| 10.98 %;| 12.09 %.|

EXAMPLE 3

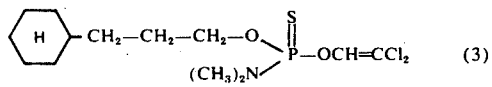

(3)

A solution, cooled to 10°C, of 300 ml of benzene and 82 g (0.33 mole) of O-(2,2-dichlorovinyl)-thionophosphoric acid ester dichloride is treated dropwise with 48 g of 3-cyclohexyl-1-propanol and 34 g of triethylamine, dissolved in 50 ml of benzene. Thereafter the batch is stirred for a half-hour at 40°C and then cooled to 10°C. 16 g of dimethylamine and 34 g of triethylamine in 200 ml of benzene are added dropwise to the cold solution. In order to achieve complete conversion, the batch is stirred for a further hour at 40°C. The salt which has separated out is filtered off, the filtrate is washed with water and subsequently dried, and thereafter the solution is concentrated under reduced pressure and subjected to "slight distillation." The product which has been subjected to "slight distillation" is extracted with petroleum ether and the extract is concentrated. A light yellow oil with a refractive index $n_D^{20}$ of 1.5062 is left. The yield is 69 g (57.5% of theory).

Calculated for $C_{13}H_{24}Cl_2NO_2PS$ (molecular weight 360.28):

|        | Cl      | N      | P      | S      |
|--------|---------|--------|--------|--------|
|        | 19.68 %;| 3.89 %;| 8.60 %;| 8.90 % |
| Found: | 19.49 %;| 3.68 %;| 8.54 %;| 8.58 %.|

EXAMPLE 4

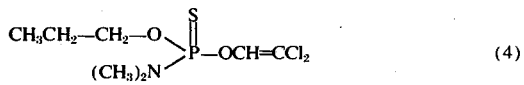

(4)

31 g of n-propanol and 40 g of pyridine, dissolved in 100 ml of methylene chloride, are added dropwise at 20°C to a solution of 123 g (0.5 mole) of O-(2,2-dichlorovinyl)-thionophosphoric acid ester dichloride in 400 ml of methylene chloride at 20°C. After completion of the dropwise addition, the batch is further stirred for 1.5 hours at 40°C. It is then cooled to 10°C and dimethylamine is passed in until the mixture reacts alkaline. To complete the reaction, the mixture is further stirred for a half-hour at 10°C and another hour at 30° to 40°C. The salt which has separated out is filtered off and the filtrate is concentrated to half under reduced pressure. It is washed once with very dilute hydrochloric acid, once with a very dilute sodium hydroxide solution and twice with water. Finally, the batch is dried over sodium sulfate. After filtering off the drying agent and concentrating the solution, an oil remains, which can be distilled. The yield is 78 g (56% of theory) of O-propyl-O-(2,2-dichlorovinyl)-N,N-dimethyl-thionophosphoric acid ester amide of boiling point 130°–135°C/1-2 mm Hg and refractive index $n_D^{20}$ of 1.4930.

Calculated for $C_7H_{14}Cl_2NO_2PS$ (278.14)

|        | Cl      | N      | P       | S       |
|--------|---------|--------|---------|---------|
|        | 25.5 %; | 5.0 %; | 11.1 %; | 11.5 %  |
| Found: | 25.3 %; | 4.4 %; | 11.4 %; | 11.0 %. |

The following compounds are prepared in a manner analogous to that described in Examples 1 to 4:

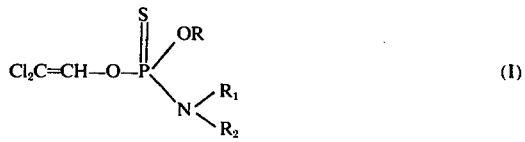

(I)

| Cpd. | R    | $R_1$ | $R_2$         | $n_D^{20}$ | Yield [% of theory] |
|------|------|-------|---------------|------------|---------------------|
| 5    | $CH_3$ | H   | $CH_3$        | 1.5189     | 54                  |
| 6    | $CH_3$ | H   | $C_2H_5$      | 1.5118     | 51                  |
| 7    | $CH_3$ | H   | $n-C_3H_7$    | 1.5088     | 63.5                |
| 8    | $CH_3$ | H   | $i-C_3H_7$    | 1.5009     | 70.5                |
| 9    | $CH_3$ | H   | $CH_2=CH-CH_2$| 1.5231     | 54                  |
| 10   | $CH_3$ | H   | $n-C_4H_9$    | 1.5081     | 50                  |
| 11   | $CH_3$ | H   | $i-C_4H_9$    | 1.5039     | 59                  |

-continued

| Cpd. | R | R₁ | R₂ | $n_D^{20}$ | Yield [% of theory] |
|---|---|---|---|---|---|
| 12 | C₂H₅ | H | n-C₃H₇ | 1.4990 | 71 |
| 13 | C₂H₅ | H | i-C₃H₇ | 1.4942 | 48.5 |
| 14 | C₂H₅ | H | CH₂=CH—CH₂ | 1.5112 | 71 |
| 15 | C₂H₅ | H | n-C₄H₉ | 1.4963 | 74 |
| 16 | C₂H₅ | H | i-C₄H₉ | 1.4970 | 45 |
| 17 | C₂H₅ | H | sec.-C₄H₉ | 1.4930 | 71 |
| 18 | C₂H₅ | C₂H₅ | C₂H₅ | 1.4900 | 45 |
| 19 | C₂H₅ | n-C₃H₇ | n-C₃H₇ | 1.4930 | 42 |
| 20 | C₂H₅ | H | CH₃O—CH₂CH₂CH₂ | 1.5022 | 55.5 |
| 21 | C₂H₅ | H | CH₃O—CH₂CH₂ | 1.4979 | 49 |
| 22 | C₂H₅ | H | C₂H₅O—CH₂CH₂CH₂ | 1.4995 | 51 |
| 23 | C₂H₅ | CH₂=CH—CH₂ | CH₂=CH—CH₂ | 1.5042 | 64.5 |
| 24 | C₂H₅ | —(CH₂)₄— | | 1.5142 | 63 |
| 25 | C₂H₅ | —(CH₂)₅— | | 1.5174 | 59 |
| 26 | C₂H₅ | —(CH₂)₂—O—(CH₂)₂— | | 1.5126 | 60 |
| 27 | n-C₃H₇ | H | CH₃ | 1.5028 | 63.5 |
| 28 | n-C₃H₇ | H | n-C₃H₇ | 1.4962 | 75 |
| 29 | n-C₃H₇ | H | i-C₃H₇ | 1.4933 | 68 |
| 30 | n-C₃H₇ | H | CH₂=CH—CH₂ | 1.5039 | 68.5 |
| 31 | n-C₃H₇ | H | n-C₄H₉ | 1.4958 | 67.5 |
| 32 | n-C₃H₇ | H | i-C₄H₉ | 1.4913 | 71.5 |
| 33 | n-C₃H₇ | H | sec.-C₄H₉ | 1.4918 | 66.5 |
| 34 | n-C₃H₇ | C₂H₅ | C₂H₅ | 1.4889 | 61.0 |
| 35 | i-C₃H₇ | H | CH₃ | 1.5107 | 71.5 |
| 36 | i-C₃H₇ | H | CH₂=CH—CH₂ | 1.5165 | 76.5 |
| 37 | Br—CH₂—CH₂ | H | CH₃ | 1.5470 | 81 |
| 38 | NC—CH₂—CH₂ | H | CH₃ | 1.5366 | 70.5 |
| 39 | n-C₄H₉ | H | CH₃ | 1.5005 | 63 |
| 40 | n-C₄H₉ | H | i-C₃H₇ | 1.4928 | 71.5 |
| 41 | n-C₄H₉ | H | CH₂=CH—CH₂ | 1.5043 | 73.5 |
| 42 | sec.-C₄H₉ | H | CH₃ | 1.5019 | 67 |
| 43 | sec.-C₄H₉ | H | i-C₃H₇ | 1.5020 | 49 |
| 44 | sec.-C₄H₉ | H | CH₂=CH—CH₂ | 1.5082 | 54 |
| 45 | i-C₄H₉ | H | CH₃ | 1.4991 | 64 |
| 46 | n-C₅H₁₁ | H | CH₃ | 1.4978 | 64 |
| 47 | i-C₅H₁₁ | H | CH₃ | 1.5002 | 49 |
| 48 | i-C₅H₁₁ | H | i-C₃H₇ | 1.4981 | 66.5 |
| 49 | n-C₅H₁₁ | CH₃ | CH₃ | 1.4920 | 83 |
| 50 | i-C₅H₁₁ | H | CH₂=CH—CH₂ | 1.5047 | 71.5 |
| 51 | n-C₆H₁₃ | H | CH₃ | 1.4971 | 73.5 |
| 52 | n-C₆H₁₃ | H | CH₂=CH—CH₂ | 1.5026 | 78.5 |
| 53 | n-C₆H₁₃ | H | 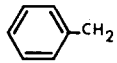 | 1.5335 | 79 |
| 54 | 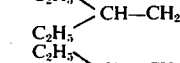 | H | CH₃ | 1.5026 | 73.5 |
| 55 | 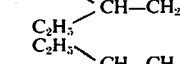 | H | i-C₃H₇ | 1.4930 | 83.5 |
| 56 | 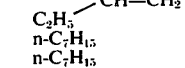 | H | CH₂=CH—CH₂ | 1.5042 | 79.5 |
| 57 | n-C₇H₁₅ | H | CH₃ | 1.4963 | 78.5 |
| 58 | n-C₇H₁₅ | H | i-C₃H₇ | 1.4915 | 85.5 |
| 59 | n-C₇H₁₅ | H | CH₂=CH—CH₂ | 1.4988 | 85.5 |
| 60 | n-C₈H₁₇ | H | CH₃ | 1.4976 | 76.5 |
| 61 | n-C₈H₁₇ | H | i-C₃H₇ | 1.4896 | 77.5 |
| 62 | n-C₈H₁₇ | H | CH₂=CH₂—CH₂ | 1.4976 | 80.5 |
| 63 | n-C₁₂H₂₅ | H | CH₃ | 1.4892 | 43 |
| 64 | CH₃O—CH₂—CH₂ | H | CH₃ | 1.5086 | 63.5 |
| 65 | CH₃O—CH₂—CH₂ | CH₃ | CH₃ | 1.5032 | 81.5 |
| 66 | CH₃O—CH₂—CH₂ | H | i-C₃H₇ | 1.5040 | 49 |
| 67 | CH₃O—CH₂—CH₂ | H | CH₂=CH—CH₂ | 1.5178 | 80 |
| 68 | CH₃CH₂O—CH₂CH₂ | H | CH₃ | 1.5078 | 49 |
| 69 | CH₃CH₂O—CH₂CH₂ | CH₃ | CH₃ | 1.4980 | 75 |
| 70 | n-C₃H₇O—CH₂CH₂ | H | CH₃ | 1.5002 | 41.5 |
| 71 | n-C₃H₇O—CH₂CH₂ | CH₃ | CH₃ | 1.5082 | 76.5 |
| 72 | n-C₄H₉O—CH₂CH₂ | H | CH₃ | 1.5028 | 47 |
| 73 |  | H | CH₃ | 1.5270 | 65 |
| 74 |  | H | i-C₃H₇ | 1.5180 | 71.5 |
| 75 |  | H | CH₂=CH—CH₂ | 1.5278 | 42.5 |
| 76 |  | H | CH₃ | 1.5250 | 48.5 |

-continued

| Cpd. | R | $R_1$ | $R_2$ | $n_D^{20}$ | Yield [% of theory] |
|---|---|---|---|---|---|
| 77 | cyclohexyl | H | i-$C_3H_7$ | 1.5170 | 45 |
| 78 | cyclohexyl | H | $CH_2$=CH—$CH_2$ | 1.5269 | 43.5 |
| 79 | cyclohexyl-$CH_2$ | H | $CH_3$ | 1.5202 | 82 |
| 80 | cyclohexyl-$CH_2$ | $CH_3$ | $CH_3$ | 1.5128 | 60 |
| 81 | cyclohexyl-$CH_2$ | H | i-$C_3H_7$ | 1.5143 | 85 |
| 82 | cyclohexyl-$CH_2$ | H | $CH_2$=CH—$CH_2$ | 1.5213 | 89 |
| 83 | cyclohexenyl-$CH_2$ | H | $CH_3$ | 1.5300 | 77.5 |
| 84 | cyclohexenyl-$CH_2$ | H | i-$C_3H_7$ | 1.5215 | 80 |
| 85 | cyclohexenyl-$CH_2$ | H | $CH_2$=CH—$CH_2$ | 1.5308 | 85 |
| 86 | cyclohexyl-$CH_2CH_2$ | H | $CH_3$ | 1.5127 | 81.5 |
| 87 | cyclohexyl-$CH_2CH_2$ | $CH_3$ | $CH_3$ | 1.5092 | 73.5 |
| 88 | cyclohexyl-$CH_2CH_2$ | H | i-$C_3H_7$ | 1.5090 | 81.5 |
| 89 | cyclohexyl-$CH_2CH_2$ | H | $CH_2$=CH—$CH_2$ | 1.5182 | 91 |
| 90 | cyclohexyl-$CH_2CH_2CH_2$ | H | $CH_3$ | 1.5145 | 76 |
| 91 | phenyl | H | $CH_3$ | 1.5678 | 82.5 |
| 92 | phenyl | H | i-$C_3H_7$ | 1.5500 | 78.5 |
| 93 | phenyl | H | $CH_2$=CH—$CH_2$ | 1.5602 | 89.5 |
| 94 | phenyl-$CH_2$ | H | $CH_3$ | 1.5632 | 55.5 |

-continued

| Cpd. | R | $R_1$ | $R_2$ | $n_D^{20}$ | Yield [% of theory] |
| --- | --- | --- | --- | --- | --- |
| 95 | 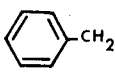-CH$_2$ | H | CH$_2$=CH—CH$_2$ | 1.5610 | 71 |
| 96 | 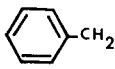-CH$_2$ | H | i-C$_3$H$_7$ | 1.5490 | 78.5 |
| 97 | 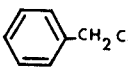-CH$_2$CH$_2$ | H | CH$_3$ | 1.5523 | 79 |
| 98 | 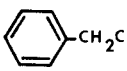-CH$_2$CH$_2$ | CH$_3$ | CH$_3$ | 1.5448 | 81 |
| 99 | 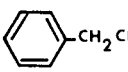-CH$_2$CH$_2$ | H | i-C$_3$H$_7$ | 1.5396 | 84.5 |
| 100 | 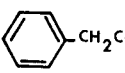-CH$_2$CH$_2$ | H | CH$_2$=CH—CH$_2$ | 1.5492 | 86 |
| 101 | 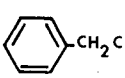-CH$_2$CH$_2$CH$_2$ | H | CH$_3$ | 1.5475 | 77.5 |
| 102 | 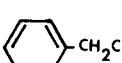-CH$_2$CH-CH$_2$ | H | i-C$_3$H$_7$ | 1.5360 | 88 |
| 103 | 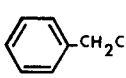-CH$_2$CH$_2$CH$_2$ | H | CH$_2$=CH—CH$_2$ | 1.5454 | 84.5 |
| 104 | (CH$_3$)$_3$C-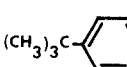- | H | CH$_3$ | 1.5472 | 87 |
| 105 | (CH$_3$)$_3$C-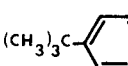- | H | i-C$_3$H$_7$ | 1.5375 | 86 |
| 106 | (CH$_3$)$_3$C-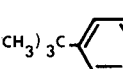- | H | CH$_2$=CH—CH$_2$ | 1.5445 | 85 |
| 107 | i-C$_4$H$_9$ | CH$_3$ | CH$_3$ | 1.4920 | 78 |
| 108 | n-C$_6$H$_{13}$ | CH$_3$ | CH$_3$ | 1.4909 | 61.5 |
| 109 | 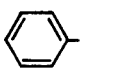- | CH$_3$ | CH$_3$ | 1.5532 | 71 |
| 110 | sec.-C$_4$H$_9$ | CH$_3$ | CH$_3$ | 1.4949 | 59 |
| 111 | n-C$_4$H$_9$ | CH$_3$ | CH$_3$ | 1.4922 | 65.5 |
| 112 | C$_2$H$_5$ | CH$_3$ | CH$_3$ | 1.4970 | 56 |
| 113 | C$_2$H$_5$ | H | C$_2$H$_5$ | 1.5349 | 57.5 |
| 114 | C$_{10}$H$_{21}$ | H | CH$_3$ | | |
| 115 | i-C$_3$H$_7$ | H | C$_2$H$_5$ | 1.4962 | 78 |
| 116 | i-C$_4$H$_9$ | H | C$_2$H$_5$ | 1.4926 | 74 |

The unexpected superiority and outstanding activity of the particular new compounds of the present invention are illustrated, without limitation, by the following examples. In some instances the compounds indicated as "known" might not actually have been shown in the art but perform similarly to other compounds actually disclosed in the art.

EXAMPLE 5

Drosophila test

Solvent: 3 parts by weight acetone

Emulsifier: 1 part by weight alkylarylpolyglycol ether

To produce a suitable preparation of active compound, 1 part by weight of the active compound is mixed with the stated amount of solvent containing the stated amount of emulsifier, and the concentrate is diluted with water to the desired concentration.

1 cc of the preparation of the active compound is applied with a pipette to a filter paper disc of 7 cm diameter. The wet disc is placed in a glass vessel containing 50 vinegar flies (*Drosophila melanogaster*) and covered with a glass plate.

After the specified periods of time, the destruction is determined as a percentage: 100% means that all the flies are killed; 0% means that none of the flies are killed.

The active compounds, their concentrations, the evaluation times and the degree of destruction can be seen from Table 2:

Table 2

| Active compound | (*Drosophila* Test) | Concentration of active compound in % | Degree of Destruction in % after 1 day |
|---|---|---|---|
| 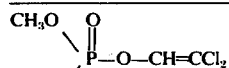 (known) | (A) | 0.0001<br>0.00001 | 100<br>0 |
| 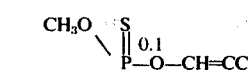 | (5) | 0.0001<br>0.00001 | 100<br>100 |
| 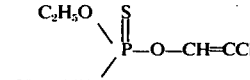 | (1) | 0.0001<br>0.00001 | 100<br>100 |
| 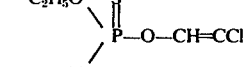 | (112) | 0.0001<br>0.00001<br>0.000001 | 100<br>100<br>100 |
| 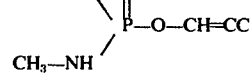 | (27) | 0.0001<br>0.00001<br>0.000001 | 100<br>100<br>90 |
| 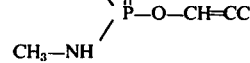 | (39) | 0.0001<br>0.00001<br>0.000001 | 100<br>100<br>30 |
| 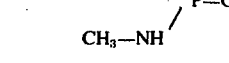 | (45) | 0.0001<br>0.00001<br>0.000001 | 100<br>100<br>100 |
| 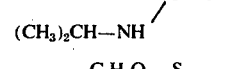 | (8) | 0.0001<br>0.00001 | 100<br>90 |
| 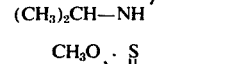 | (13) | 0.0001<br>0.00001 | 100<br>100 |
|  | (6) | 0.0001<br>0.00001<br>0.000001 | 100<br>100<br>70 |
| 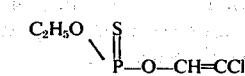 | (21) | 0.0001<br>0.00001<br>0.000001 | 100<br>100<br>50 |
| 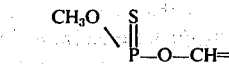 | (18) | 0.0001<br>0.00001<br>0.000001 | 100<br>100<br>50 |
|  | (7) | 0.0001<br>0.00001 | 100<br>100 |

Table 2-continued
(*Drosophila* Test)

| Active compound | | Concentration of active compound in % | Degree of Destruction in % after 1 day |
|---|---|---|---|
| 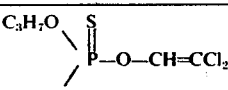 | (29) | 0.0001<br>0.00001<br>0.000001 | 100<br>100<br>80 |
| 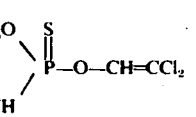 | (15) | 0.0001<br>0.00001 | 100<br>·98 |
| 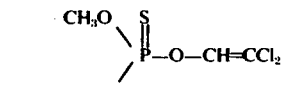 | (11) | 0.0001<br>0.00001 | 100<br>100 |
| 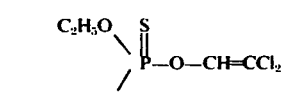 | (16) | 0.0001<br>0.00001 | 100<br>100 |
| 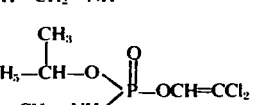<br>(known) (B) | | 0.1<br>0.01<br>0.001 | 100<br>95<br>0 |
| 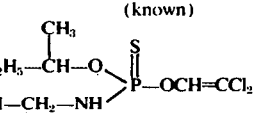 | (44) | 0.1<br>0.01<br>0.001 | 100<br>100<br>75 |
| 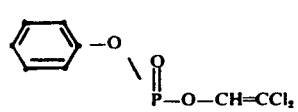<br>(known) (C) | | 0.1 | 0 |
| 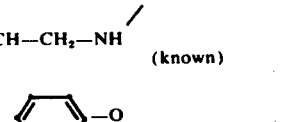 | (93) | 0.1<br>0.01 | 100<br>90 |
| 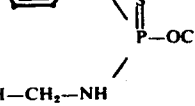<br>(known) (D) | | 0.0001<br>0.00001 | 100<br>0 |
| 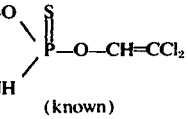 | (115) | 0.0001<br>0.00001 | 100<br>100 |

EXAMPLE 6

Myzus test (contact action)

Solvent: 3 parts by weight acetone
Emulsifier: 1 part by weight alkylaryl polyglycol ether To produce a suitable preparation of active compound, 1 part by weight of the active compound is mixed with the stated amount of solvent containing the stated amount of emulsifier and the concentrate is diluted with water to the desired concentration.

Cabbage plants (*Brassica oleracea*) which have been heavily infested with peach aphids (*Myzus persicae*) are sprayed with the preparation of the active compound until dripping wet.

After the specified periods of time, the degree of destruction is determined as a percentage: 100% means that all the aphids are killed whereas 0% means that none of the aphids are killed.

The active compounds, the concentrations of the active compounds, the evaluation times and the results can be seen from the following Table 3:

Table 3

(Myzus Test)

| Active compound | Concentration of active compound in % | Degree of destruction in % after 1 day |
|---|---|---|
| $(CH_3O)_2P(O)-O-CH=CCl_2$ (known) (A) | 0.1<br>0.01<br>0.001 | 100<br>70<br>0 |
| $CH_3O-CH_2-CH_2O$, $CH_3-NH$ — $P(S)-O-CH=CCl_2$ (64) | 0.1<br>0.01<br>0.001 | 100<br>100<br>95 |
| $C_2H_5O-CH_2-CH_2O$, $CH_3-NH$ — $P(S)-O-CH=CCl_2$ (68) | 0.1<br>0.01<br>0.001 | 100<br>100<br>99 |
| $C_3H_7O-CH_2-CH_2O$, $CH_3-NH$ — $P(S)-O-CH=CCl_2$ (70) | 0.1<br>0.01<br>0.001 | 100<br>99<br>85 |
| $C_4H_9O-CH_2-CH_2O$, $CH_3-NH$ — $P(S)-O-CH=CCl_2$ (72) | 0.1<br>0.01<br>0.001 | 100<br>100<br>99 |
| $(CH_3)_2CH-CH_2-CH_2O$, $CH_3-NH$ — $P(S)-O-CH=CCl_2$ (47) | 0.1<br>0.01<br>0.001 | 100<br>100<br>70 |
| $(C_2H_5)_2CH-CH_2O$, $CH_3-NH$ — $P(S)-O-CH=CCl_2$ (54) | 0.1<br>0.01<br>0.001 | 100<br>99<br>55 |
| furfuryl-O, $CH_3-NH$ — $P(S)-O-CH=CCl_2$ (73) | 0.1<br>0.01 | 100<br>100 |
| furfuryl-O, $CH_2=CH-CH_2-NH$ — $P(S)-O-CH=CCl_2$ (75) | 0.1<br>0.01 | 100<br>98 |
| $C_4H_9-O$, $C_4H_9-NH$ — $P(S)-O-CH=CCl_2$ (known) (D) | 0.1<br>0.01 | 50<br>0 |
| $(CH_3)_2CH-O$, $C_2H_5-NH$ — $P(S)-O-CH=CCl_2$ (115) | 0.1<br>0.01 | 100<br>98 |
| $(CH_3)_2CH-CH_2-O$, $C_2H_5-NH$ — $P(S)-O-CH=CCl_2$ (116) | 0.1<br>0.01 | 100<br>100 |

EXAMPLE 7

Tetranychus test/resistant

Solvent: 3 parts by weight acetone
Emulsifier: 1 part by weight alkylaryl polyglycol ether To produce a suitable preparation of active compound, 1 part by weight of the active compound is mixed with the stated amount of solvent containing the stated amount of emulsifier and the concentrate so obtained is diluted with water to the desired concentration.

Bean plants (*Phaseolus vulgaris*), which have a height of approximately 10–30 cm., are sprayed with the preparation of the active compound until dripping wet. These bean plants are heavily infested with spider mites (*Tetranychus urticae*) in all stages of development.

After the specified period of time, the effectiveness of the preparation of active compound is determined by counting the dead mites. The degree of destruction thus obtained is expressed as a percentage: 100% means that all the spider mites are killed whereas 0% means that none of the spider mites are killed whereas 0% means that none of the spider mites are killed.

The active compounds, the concentrations of the active compounds, the evaluation times and the results can be seen from the following Table 4:

Table 4
(*Tetranychus* Test)

| Active compound | Concentration of active compound in % | Degree of destruction in % after 8 days |
|---|---|---|
| 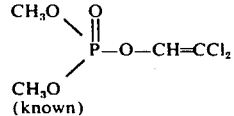 (A) (known) | 0.1<br>0.01 | 20<br>0 |
| 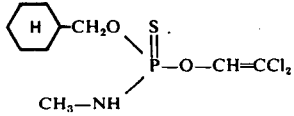 (79) | 0.1 | 98 |
| 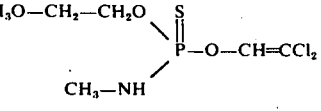 (64) | 0.1 | 100 |
| 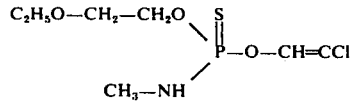 (68) | 0.1<br>0.01 | 100<br>50 |
| 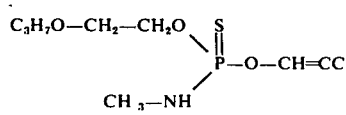 (70) | 0.1<br>0.01 | 100<br>50 |
| 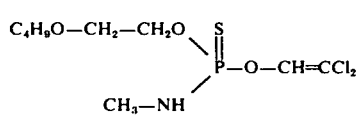 (72) | 0.1<br>0.01 | 100<br>98 |
| 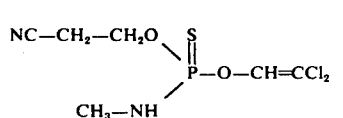 (38) | 0.1 | 98 |
| 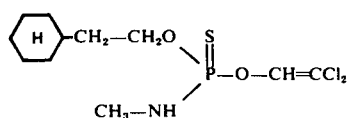 (86) | 0.1<br>0.01 | 100<br>70 |
| 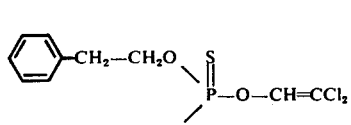 (97) | 0.1<br>0.01 | 100<br>98 |

Table 4-continued (*Tetranychus* Test)

| Active compound | Concentration of active compound in % | Degree of destruction in % after 8 days |
|---|---|---|
| $C_3H_7O$–P(=S)(O–CH=CCl$_2$)–NH–CH$_3$ (27) | 0.1 | 98 |
| cyclohexyl-CH$_2$–CH$_2$–CH$_2$O–P(=S)(O–CH=CCl$_2$)–NH–CH$_3$ (90) | 0.1 | 98 |
| C$_6$H$_5$–CH$_2$–CH$_2$–CH$_2$O–P(=S)(O–CH=CCl$_2$)–NH–CH$_3$ (101) | 0.1<br>0.01 | 100<br>98 |
| $C_4H_9O$–P(=S)(O–CH=CCl$_2$)–NH–CH$_3$ (39) | 0.1 | 100 |
| $C_5H_{11}O$–P(=S)(O–CH=CCl$_2$)–NH–CH$_3$ (46) | 0.1<br>0.01 | 100<br>70 |
| $(CH_3)_2CH$–CH$_2$–CH$_2$O–P(=S)(O–CH=CCl$_2$)–NH–CH$_3$ (47) | 0.1 | 98 |
| $C_6H_{13}O$–P(=S)(O–CH=CCl$_2$)–NH–CH$_3$ (51) | 0.1<br>0.01 | 98<br>70 |
| $C_6H_{13}O$–P(=S)(O–CH=CCl$_2$)–NH–CH$_2$–C$_6$H$_5$ (53) | 0.1 | 98 |
| $C_7H_{15}O$–P(=S)(O–CH=CCl$_2$)–NH–CH$_3$ (57) | 0.1<br>0.01 | 100<br>50 |
| $C_{10}H_{21}O$–P(=S)(O–CH=CCl$_2$)–NH–CH$_3$ (114) | 0.1<br>0.01 | 98<br>50 |
| C$_6$H$_5$O–P(=S)(O–CH=CCl$_2$)–NH–CH$_3$ (91) | 0.1<br>0.01 | 100<br>50 |
| cyclohexyl-CH$_2$–CH$_2$O–P(=S)(O–CH=CCl$_2$)–NH–CH$_2$–CH=CH$_2$ (89) | 0.1 | 98 |

Table 4-continued
(*Tetranychus* Test)
| Active compound | Concentration of active compound in % | Degree of destruction in % after 8 days |
|---|---|---|
| 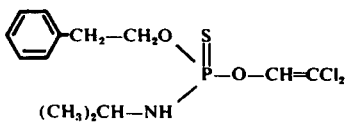 (99) | 0.1<br>0.01 | 98<br>50 |
| 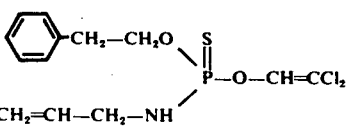 (100) | 0.1<br>0.01 | 98<br>50 |
| 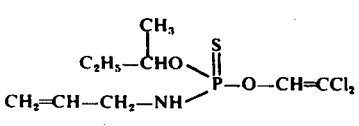 (44) | 0.1 | 98 |
| 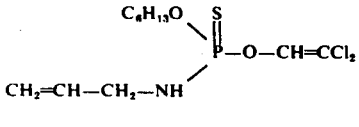 (52) | 0.1 | 100 |
| 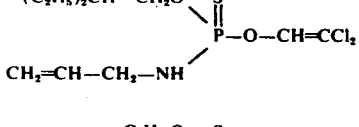 (56) | 0.1 | 98 |
| 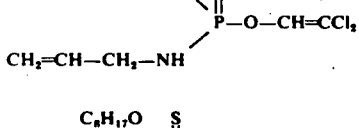 (59) | 0.1 | 98 |
| 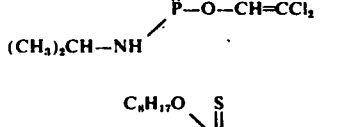 (61) | 0.1 | 98 |
| 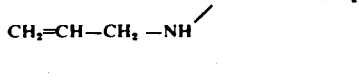 (62) | 0.1<br>0.01 | 98<br>50 |
| 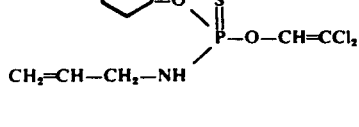 (75) | 0.1 | 98 |
| 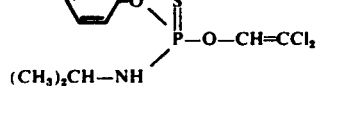 (92) | 0.1 | 98 |
| 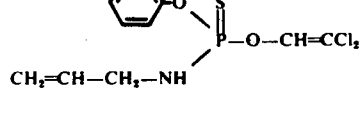 (93) | 0.1 | 98 |

Table 4-continued

| Active compound | (*Tetranychus* Test) Concentration of active compound in % | Degree of destruction in % after 8 days |
|---|---|---|
| 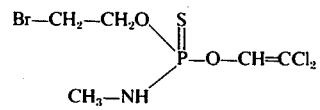 (93) | 0.1 | 98 |
| 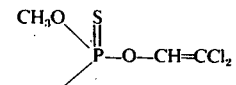 (37) | 0.1 | 100 |
| (10) | | |

EXAMPLE 8

Critical concentration test

Test menatode: *Meloidogyne incognita*
Solvent: 3 parts by weight acetone
Emulsifier: 1 part by weight alkylarylpolyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is heavily infested with the test nematodes. The concentration of the active compound in the preparation is of practically no importance; only the amount of active compound per unit volume of soil, which is given in p.p.m., is decisive. The soil is filled with pots, lettuce is sown in and the pots are kept at a greenhouse temperature of 27°C. After 4 weeks, the lettuce roots are examined for infestation with nematodes, and the degree of destruction of the active compound is determined as a percentage. The degree of effectiveness is 100% when infestation is completely avoided; it is 0% when the infestation is exactly the same as in the case of the control plants in untreated soil which has been infested in the same manner.

The active compounds, the amounts applied and the results can be seen from the following Table 5:

Table 5

| Active compound | (*Meloidogyne incognita* Test) Degree of destruction in % for an active compound concentration of | | | | | | |
|---|---|---|---|---|---|---|---|
| | 20 | 10 | 5 | 2.5 | 1.25 | 0.625 | ppm |
| 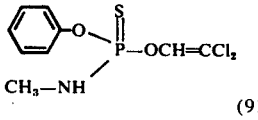 (91) | 100 | 99 | 50 | | | | |
| 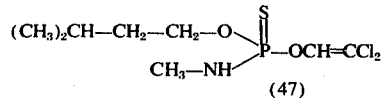 (47) | 100 | 98 | 95 | 50 | | | |
| 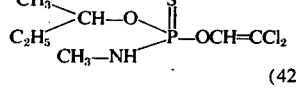 (42) | 100 | 100 | 98 | 50 | | | |
| 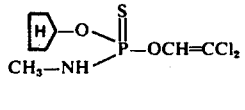 (15) | 100 | 98 | 75 | 50 | | | |
| 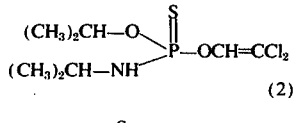 (2) | 100 | 98 | 65 | | | | |
| 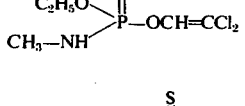 (1) | 100 | 100 | 98 | 95 | 90 | 90 | |
| 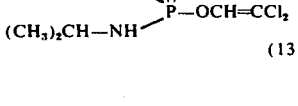 (13) | 100 | 100 | 100 | 98 | 90 | 50 | |

Table 5-continued
(*Meloidogyne incognita* Test)
| Active compound | Degree of destruction in % for an active compound concentration of | | | | | | |
|---|---|---|---|---|---|---|---|
| | 20 | 10 | 5 | 2.5 | 1.25 | 0.625 | ppm |
| 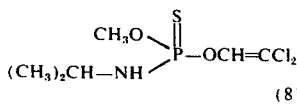 (8) | 100 | 99 | 95 | 75 | 50 | 0 | |
| 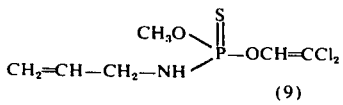 (9) | 100 | 99 | 95 | 75 | 50 | 0 | |
| 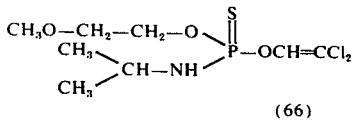 (66) | 100 | 98 | 95 | 75 | 50 | 0 | |
| 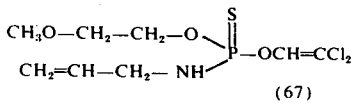 (67) | 99 | 96 | 90 | 50 | | | |
| 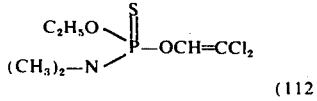 (112) | 100 | 98 | 95 | 75 | 0 | | |
| 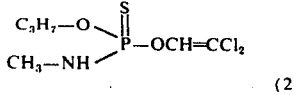 (27) | 100 | 100 | 100 | 100 | 90 | 50 | |
| 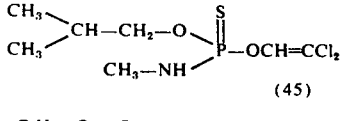 (45) | 100 | 100 | 95 | 75 | | | |
| 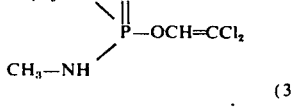 (39) | 100 | 100 | 98 | 75 | 0 | | |
| 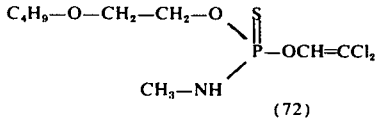 (72) | 100 | 90 | 50 | | | | |
| 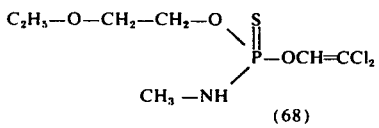 (68) | 100 | 100 | 98 | 75 | 50 | 0 | |
| 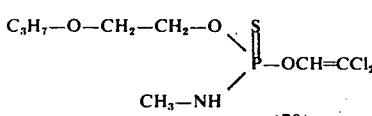 (70) | 100 | 99 | 95 | 50 | | | |
| 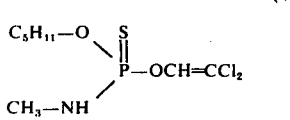 (46) | 100 | 98 | 95 | 50 | 0 | | |
| 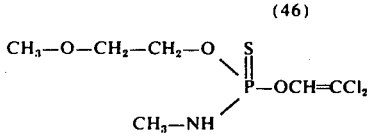 (64) | 100 | 100 | 98 | 50 | | | |

Table 5-continued
(*Meloidogyne incognita* Test)
| Active compound | Degree of destruction in % for an active compound concentration of | | | | | | |
|---|---|---|---|---|---|---|---|
| | 20 | 10 | 5 | 2.5 | 1.25 | 0.625 | ppm |
| 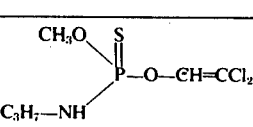 (7) | 100 | 100 | | | | | |
| 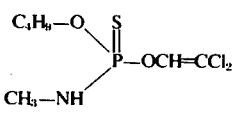 (39) | 100 | 100 | 98 | 75 | 0 | | |
| 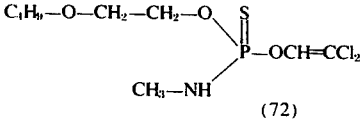 (72) | 100 | 99 | 50 | | | | |
| 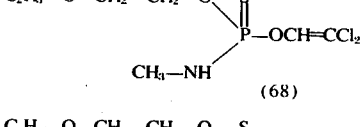 (68) | 100 | 100 | 98 | 75 | 50 | 0 | |
| 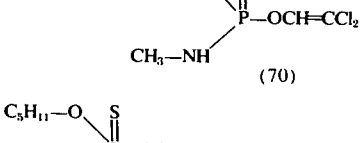 (70) | 100 | 99 | 95 | 50 | | | |
| 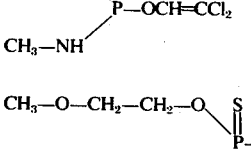 (46) | 100 | 98 | 95 | 50 | 0 | | |
| 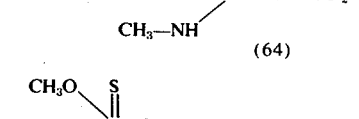 (64) | 100 | 100 | 98 | 50 | | | |
| 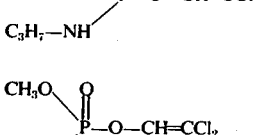 (7) | 100 | 100 | | | | | |
| 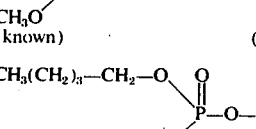 (known) (A) | 0 | | | | | | |
| 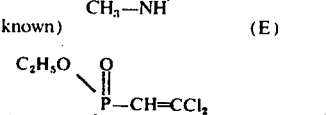 (known) (E) | 0 | | | | | | |
| 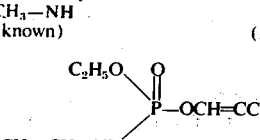 (known) (F) | 0 | | | | | | |
| 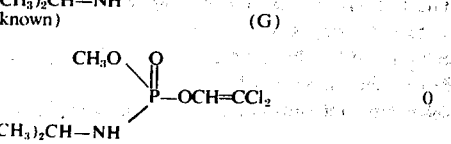 (known) (G) | 0 | | | | | | |
| 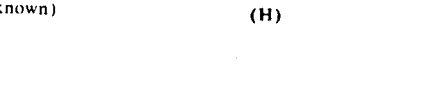 (known) (H) | 0 | | | | | | |

Table 5-continued
(*Meloidogyne incognita* Test)

| Active compound | Degree of destruction in % for an active compound concentration of | | | | | |
|---|---|---|---|---|---|---|
| | 20 | 10 | 5 | 2.5 | 1.25 | 0.625 ppm |

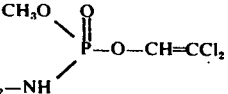

(K) (known) — 0

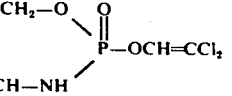

(L) (known) — 0

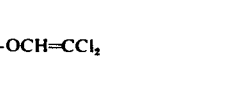

(M) (known) — 0

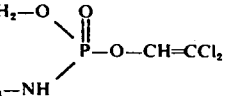

(N) (known) — 0

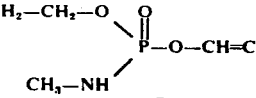

(P) (known) — 0

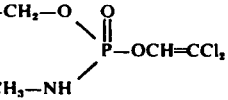

(Q) (known) — 0

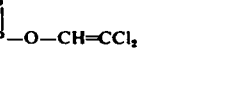

(D) (known) — 0

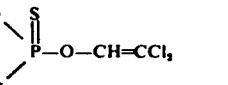

(115) — 100

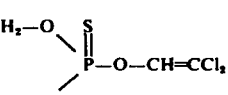

(116) — 100

EXAMPLE 9

Critical concentration test/soil insects

Test insect: *Tenebrio molitor* larvae
Solvent: 3 parts by weight acetone
Emulsifier: 1 part by weight alkylarylpolyglycol ether To produce a suitable preparation of active compound, 1 part by weight of active compound is mixed with the stated amount of solvent, the stated amount of emulsifier is added and the concentrate is diluted with water to the desired concentration. The preparation of active compound is intimately mixed with soil. The concentration of the active compound in the preparation is of practically no importance; only the amount by weight of active compound per unit volume of soil, which is given in p.p.m. (for example mg/l), is decisive. The soil is filled with pots and the pots are left to stand at room temperature. After 24 hours, the test insects are put into the treated soil and, after a further 48 hours, the degree of effectiveness of the active compound is determined as a percentage by counting the dead and living test insects. The degree of effectiveness is 100% when all the test insects have been killed; it is 0% when exactly as many test insects are still alive as in the case of the control.

The active compounds, the amounts applied and the results can be seen from the following Table 6:

Table 6
(*Tenebrio molitor* larvae in the soil)

| Active compound | Degree of destruction in % for an active compound concentration of | | | | | | |
|---|---|---|---|---|---|---|---|
| | 20 | 10 | 5 | 2.5 | 1.25 | 0.625 | ppm |
| 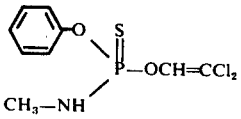 (91) | 100 | 100 | 100 | 100 | 50 | | |
| 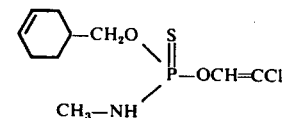 (83) | 100 | 95 | 70 | 50 | | | |
| 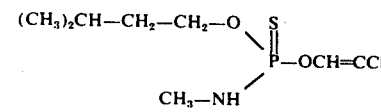 (47) | 100 | 100 | 100 | 100 | 100 | 100 | |
| 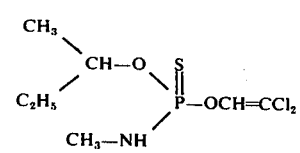 (42) | 100 | 100 | 100 | 100 | 100 | 95 | |
| 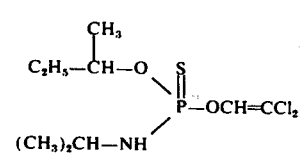 (43) | 100 | 100 | 100 | 50 | | | |
| 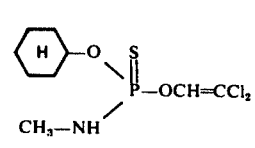 (76) | 100 | 100 | 100 | 100 | 100 | 90 | |
| 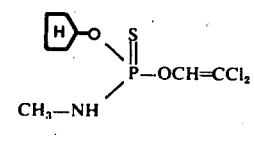 (73) | 100 | 100 | 100 | 100 | 100 | 50 | |
| 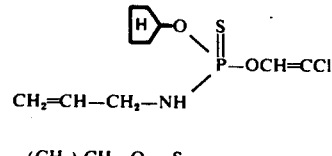 (75) | 100 | 100 | 95 | 90 | 50 | | |
| 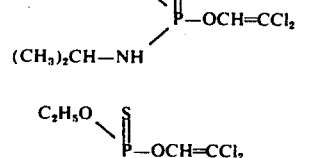 (2) | 100 | 100 | 100 | 98 | 50 | | |
| 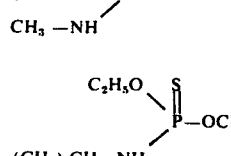 (1) | 100 | 100 | 100 | 100 | 50 | | |
|  (13) | 100 | 100 | 100 | 100 | 100 | 100 | |

Table 6-continued
(*Tenebrio molitor* larvae in the soil)

| Active compound | \multicolumn{6}{c}{Degree of destruction in % for an active compound concentration of} | |
|---|---|---|---|---|---|---|---|
| | 20 | 10 | 5 | 2.5 | 1.25 | 0.625 | ppm |

| Active compound | 20 | 10 | 5 | 2.5 | 1.25 | 0.625 |
|---|---|---|---|---|---|---|
| (14) $CH_2=CH-CH_2-NH$, $C_2H_5O$, $S$, $P-OCH=CCl_2$ | 100 | 100 | 95 | 70 | | |
| (5) $CH_3-NH$, $CH_3O$, $S$, $P-OCH=CCl_2$ | 100 | 100 | 100 | 100 | 100 | 100 |
| (8) $(CH_3)_2CH-NH$, $CH_3O$, $S$, $P-OCH=CCl_2$ | 100 | 100 | 100 | 95 | 50 | |
| (9) $CH_2=CH-CH_2-NH$, $CH_3O$, $S$, $P-OCH=CCl_2$ | 100 | 100 | 100 | 100 | 100 | 50 |
| (112) $(CH_3)_2N$, $C_2H_5O$, $S$, $P-OCH=CCl_2$ | 100 | 100 | 100 | 95 | 50 | |
| (4) $(CH_3)_2N$, $C_3H_7-O$, $S$, $P-OCH=CCl_2$ | 100 | 100 | 100 | 98 | 70 | 50 |
| (111) $(CH_3)_2N$, $C_4H_9-O$, $S$, $P-OCH=CCl_2$ | 100 | 100 | 98 | 98 | 90 | 30 |
| (109) $(CH_3)_2N$, $C_6H_5-O$, $S$, $P-OCH=CCl_2$ | 100 | 100 | 100 | 95 | 50 | |
| (107) $(CH_3)_2N$, $(CH_3)_2CH-CH_2O$, $S$, $P-OCH=CCl_2$ | 100 | 100 | 100 | 90 | 50 | |
| (49) $(CH_3)_2N$, $C_5H_{11}-O$, $S$, $P-OCH=CCl_2$ | 100 | 100 | 95 | 20 | | |
| (69) $(CH_3)_2N$, $CH_3-CH_2-O-CH_2-CH_2-O$, $S$, $P-OCH=CCl_2$ | 100 | 98 | 50 | | | |
| (65) $(CH_3)_2N$, $CH_3-O-CH_2-CH_2-O$, $S$, $P-OCH=CCl_2$ | 100 | 100 | 50 | | | |

Table 6-continued (*Tenebrio molitor* larvae in the soil)

| Active compound | | 20 | 10 | 5 | 2.5 | 1.25 | 0.625 ppm |
|---|---|---|---|---|---|---|---|
| Cyclohexyl-CH$_2$-O-P(=S)(N(CH$_3$)$_2$)-OCH=CCl$_2$ (80) | | 100 | 100 | 50 | | | |
| Phenyl-CH$_2$-CH$_2$-O-P(=S)(N(CH$_3$)$_2$)-OCH=CCl$_2$ (87) | | 100 | 98 | 70 | 50 | | |
| C$_3$H$_7$-O-CH$_2$-CH$_2$-O-P(=S)(N(CH$_3$)$_2$)-OCH=CCl$_2$ (71) | | 100 | 100 | 93 | 90 | | |
| C$_3$H$_7$-O-P(=S)(NHCH$_3$)-OCH=CCl$_2$ (27) | | 100 | 100 | 100 | 100 | 95 | 50 |
| (CH$_3$)$_2$CH-CH$_2$-O-P(=S)(NHCH$_3$)-OCH=CCl$_2$ (45) | | 100 | 100 | 100 | 100 | 95 | 95 |
| C$_4$H$_9$-O-P(=S)(NHCH$_3$)-OCH=CCl$_2$ (39) | | 100 | 100 | 100 | 100 | 100 | 98 |
| C$_4$H$_9$-O-CH$_2$-CH$_2$-O-P(=S)(NHCH$_3$)-OCH=CCl$_2$ (72) | | 100 | 100 | 95 | 70 | | |
| C$_2$H$_5$-O-CH$_2$-CH$_2$-O-P(=S)(NHCH$_3$)-OCH=CCl$_2$ (68) | | 100 | 100 | 100 | 98 | 70 | 30 |
| C$_3$H$_7$-O-CH$_2$-O-P(=S)(NHCH$_3$)-OCH=CCl$_2$ (70) | | 100 | 100 | 100 | 75 | | |
| C$_5$H$_{11}$-O-P(=S)(NHCH$_3$)-OCH=CCl$_2$ (46) | | 100 | 100 | 100 | 95 | 30 | |
| CH$_3$-O-CH$_2$-CH$_2$-O-P(=S)(NHCH$_3$)-OCH=CCl$_2$ (64) | | 100 | 100 | 100 | 98 | 50 | |
| sec.-C$_4$H$_9$O-P(=S)(N(CH$_3$)$_2$)-OCH=CCl$_2$ (110) | | 100 | 100 | 70 | 50 | | |
| CH$_3$O-P(=S)(NHC$_3$H$_7$)-O-CH=CCl$_2$ (7) | | 100 | 100 | | | | |

Table 6-continued
(*Tenebrio molitor* larvae in the soil)

| Active compound | | Degree of destruction in % for an active compound concentration of | | | | | |
|---|---|---|---|---|---|---|---|
| | | 20 | 10 | 5 | 2.5 | 1.25 | 0.625 ppm |
| $\begin{array}{c}CH_3O\\ \phantom{xx}\diagdown\\ CH_3O\end{array}\!\!P(=O)\!-\!O\!-\!CH\!=\!CCl_2$ (known) (A) | | 0 | | | | | |
| $\begin{array}{c}C_4H_9\!-\!O\\ \phantom{xx}\diagdown\\ C_4H_9\!-\!NH\end{array}\!\!P(=S)\!-\!O\!-\!CH\!=\!CCl_2$ (known) (D) | | 0 | | | | | |
| $\begin{array}{c}CH_3\\ \phantom{x}\diagdown\\ CH_3\end{array}\!\!CH\!-\!O\!\diagdown\!P(=S)\!-\!O\!-\!CH\!=\!CCl_2$ $C_2H_5\!-\!NH$ (115) | | 100 | | | | | |
| $\begin{array}{c}CH_3\\ \phantom{x}\diagdown\\ CH_3\end{array}\!\!CH\!-\!CH_2\!-\!O\!\diagdown\!P(=S)\!-\!O\!-\!CH\!=\!CCl_2$ $C_2H_5\!-\!NH$ (116) | | 100 | | | | | |
| $\begin{array}{c}(CH_3)_2CH\!-\!O\\ \phantom{xx}\diagdown\\ (CH_3)_2CH\!-\!NH\end{array}\!\!P(=O)\!-\!OCH\!=\!CCl_2$ (known) (R) | | 90 | 50 | 0 | | | |
| $\begin{array}{c}C_2H_5O\!-\!CH_2\!-\!CH_2\!-\!O\\ \phantom{xxxxxx}\diagdown\\ CH_3\!-\!NH\end{array}\!\!P(=O)\!-\!OCH\!=\!CCl_2$ (known) (Q) | | 0 | | | | | |
| $\begin{array}{c}C_3H_7\!-\!O\!-\!CH_2\!-\!CH_2\!-\!O\\ \phantom{xxxxxx}\diagdown\\ CH_3NH\end{array}\!\!P(=O)\!-\!OCH\!=\!CCl_2$ (known) (S) | | 0 | | | | | |

EXAMPLE 10

Critical concentration test/soil insects

Test insect: cabbage root fly maggots (*Phorbia brassicae*)
Solvent: 3 parts by weight acetone
Emulsifier: 1 part by weight alkylarylpolyglycol ether To produce a suitable preparation of active compound, 1 part by weight of active compound is mixed with the stated amount of solvent, the stated amount of emulsifier is added and the concentrate is diluted with water to the desired concentration. The preparation of active compound is intimately mixed with soil. The concentration of the active compound in the preparation is of practically no importance; only the amount by weight of active compound per unit volume of soil, which is given in p.p.m. (for example mg/l), is decisive. The soil is filled into pots and the pots are left to stand at room temperature. After 24 hours, the test insects are put into the treated soil and, after a further 48 hours, the degree of effectiveness of the active compound is determined as a percentage by counting the dead and living test insects. The degree of effectiveness is 100% when all the test insects have been killed; it is 0% when exactly as many test insects are still alive as in the case of the control.

The active compounds, the amounts applied and the results can be seen from the following Table 7:

Table 7

(*Phorbia brassicae* maggots in the soil)

| Active compound | ppm | \multicolumn{7}{c}{Degree of destruction in % for an active compound concentration of} |
|---|---|---|---|---|---|---|---|---|
| | | 20 | 10 | 5 | 2.5 | 1.25 | 0.625 | 0.3125 |
| $C_6H_{13}$—O—P(=S)(OCH=CCl$_2$)—NH—CH$_2$—CH=CH$_2$ (52) | | 100 | 100 | 100 | 90 | | | |
| $C_6H_{13}$—O—P(=S)(OCH=CCl$_2$)—NH—CH$_2$—C$_6$H$_5$ (53) | | 100 | 100 | 100 | 90 | | | |
| $C_6H_{13}$—O—P(=S)(OCH=CCl$_2$)—NH—CH$_3$ (51) | | 100 | 100 | 100 | 90 | | | |
| C$_6$H$_5$—O—P(=S)(OCH=CCl$_2$)—NH—CH$_3$ (91) | | 100 | 100 | 100 | 100 | 95 | 50 | |
| C$_6$H$_5$—CH$_2$—CH$_2$—CH$_2$—O—P(=S)(OCH=CCl$_2$)—NH—CH$_3$ (101) | | 100 | 100 | 100 | 50 | | | |
| C$_6$H$_5$—CH$_2$—O—P(=S)(OCH=CCl$_2$)—NH—CH$_3$ (84) | | 100 | 100 | 100 | 30 | | | |
| $C_7H_{15}$O—P(=S)(OCH=CCl$_2$)—NH—CH$_3$ (57) | | 100 | 100 | 100 | 50 | | | |
| $C_8H_{17}$O—P(=S)(OCH=CCl$_2$)—NH—CH$_3$ (60) | | 100 | 100 | 100 | 98 | 50 | | |
| cyclo-C$_6$H$_{11}$—CH$_2$—CH$_2$—O—P(=S)(OCH=CCl$_2$)—NH—CH$_3$ (86) | | 100 | 100 | 100 | 50 | | | |
| C$_6$H$_5$—CH$_2$—CH$_2$—O—P(=S)(OCH=CCl$_2$)—NH—CH$_3$ (97) | | 100 | 100 | 98 | 90 | 50 | | |
| C$_6$H$_5$—CH$_2$—CH$_2$—O—P(=S)(OCH=CCl$_2$)—NH—CH(CH$_3$)$_2$ (99) | | 100 | 100 | 95 | 50 | | | |

Table 7-continued
(*Phorbia brassicae* maggots in the soil)
| Active compound | ppm | Degree of destruction in % for an active compound concentration of | | | | | |
|---|---|---|---|---|---|---|---|
| | | 20 | 10 | 5 | 2.5 | 1.25 | 0.625 | 0.3125 |
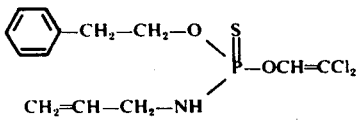
(100)
100 100 100 50
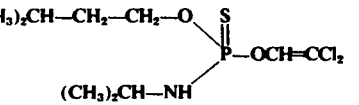
(48)
100 100 50
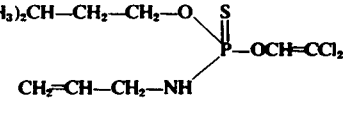
(50)
100 98 50
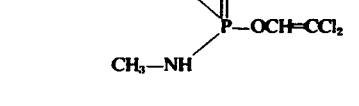
(47)
100 100 100 98 50
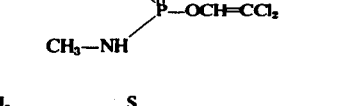
(54)
100 100 100 50
(42)
100 100 100 100 100 100
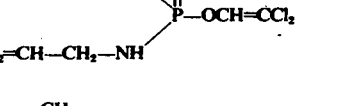
(44)
100 100 50
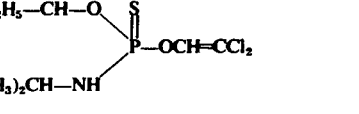
(43)
100 100 75
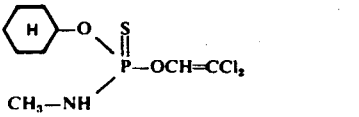
(76)
100 100 95 90 50
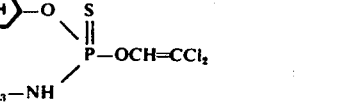
(73)
100 100 100 75 0
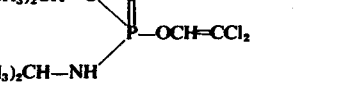
(2)
100 100 100 100 100 100
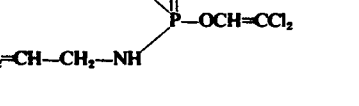
(36)
100 100 100 100 80 50

Table 7-continued

| Active compound | | (*Phorbia brassicae* maggots in the soil) Degree of destruction in % for an active compound concentration of | | | | | | |
|---|---|---|---|---|---|---|---|---|
| | ppm | 20 | 10 | 5 | 2.5 | 1.25 | 0.625 | 0.3125 |
| cyclohexyl-CH₂O, CH₃—NH, P(=S)—OCH=CCl₂ (79) | | 100 | 100 | 100 | 75 | 0 | | |
| C₂H₅O, CH₃—NH, P(=S)—OCH=CCl₂ (1) | | 100 | 100 | 100 | 100 | 100 | 100 | |
| C₂H₅O, (CH₃)₂CH—NH, P(=S)—OCH=CCl₂ (13) | | 100 | 100 | 100 | 100 | 100 | 100 | 95 |
| C₂H₅O, CH₂=CH—CH₂—NH, P(=S)—OCH=CCl₂ (14) | | 100 | 100 | 100 | 100 | 100 | 100 | |
| CH₃O, CH₃—NH, P(=S)—OCH=CCl₂ (5) | | 100 | 100 | 100 | 100 | 100 | 100 | |
| CH₃O, (CH₃)₂CH—NH, P(=S)—OCH=CCl₂ (8) | | 100 | 100 | 100 | 100 | 100 | 100 | |
| CH₃O, CH₂=CH—CH₂—NH, P(=S)—OCH=CCl₂ (9) | | 100 | 100 | 100 | 100 | 100 | 100 | |
| CH₃O—CH₂—CH₂—O, (CH₃)₂CH—NH, P(=S)—OCH=CCl₂ (66) | | 100 | 100 | 95 | 90 | 50 | | |
| C₂H₅O, (CH₃)₂N, P(=S)—OCH=CCl₂ (112) | | 100 | 100 | 100 | 100 | 100 | 100 | |
| i-C₃H₇—O, (CH₃)₂N, P(=S)—OCH=CCl₂ (4) | | 100 | 100 | 100 | 100 | 100 | 100 | |
| C₄H₉—O, (CH₃)₂N, P(=S)—OCH=CCl₂ (111) | | 100 | 100 | 100 | 99 | 95 | 50 | |
| C₆H₅—O, (CH₃)₂N, P(=S)—OCH=CCl₂ (109) | | 100 | 100 | 100 | 75 | | | |

Table 7-continued
| Active compound | ppm | (*Phorbia brassicae* maggots in the soil) Degree of destruction in % for an active compound concentration of | | | | | | |
|---|---|---|---|---|---|---|---|---|
| | | 20 | 10 | 5 | 2.5 | 1.25 | 0.625 | 0.3125 |
| 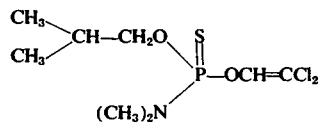 (107) | | 100 | 100 | 100 | 100 | 100 | 100 | |
| 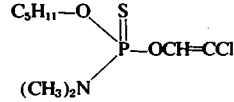 (49) | | 100 | 100 | 95 | 50 | | | |
| 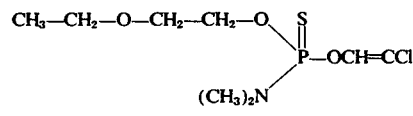 (69) | | 100 | 100 | 100 | 80 | | | |
| 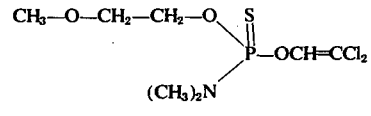 (65) | | 100 | 95 | 50 | | | | |
| 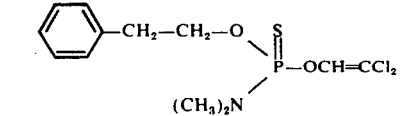 (87) | | 100 | 100 | 100 | 50 | | | |
| 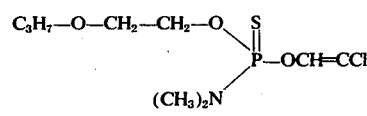 (71) | | 100 | 100 | 100 | 75 | | | |
| 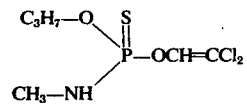 (27) | | 100 | 100 | 100 | 100 | 100 | 100 | |
| 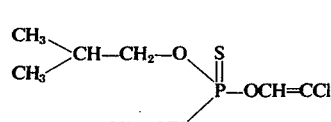 (45) | | 100 | 100 | 100 | 100 | 100 | 100 | |
| 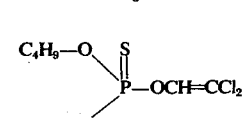 (39) | | 100 | 100 | 100 | 100 | 100 | 100 | 98 |
| 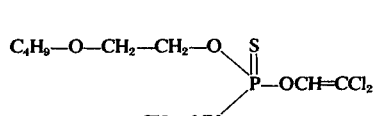 (72) | | 100 | 100 | 100 | 100 | 100 | 100 | 95 |
| 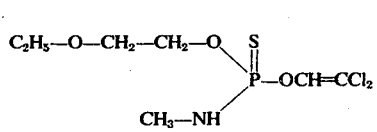 (68) | | 100 | 100 | 100 | 100 | 100 | 95 | 50 |
| 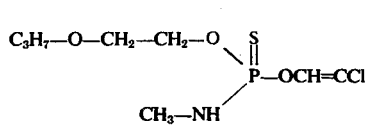 (70) | | 100 | 100 | 100 | 100 | 100 | 75 | 0 |

Table 7-continued (*Phorbia brassicae* maggots in the soil)

| Active compound | ppm | \multicolumn{7}{c}{Degree of destruction in % for an active compound concentration of} |
|---|---|---|---|---|---|---|---|---|
| | | 20 | 10 | 5 | 2.5 | 1.25 | 0.625 | 0.3125 |
| $C_5H_{11}-O$, $P(=S)-OCH=CCl_2$, $CH_3-NH$ (46) | | 100 | 100 | 100 | 100 | 50 | | |
| $CH_3-O-CH_2-CH_2-O$, $P(=S)-OCH=CCl_2$, $CH_3-NH$ (64) | | 100 | 100 | 100 | 100 | 100 | 80 | |
| $NC-CH_2-CH_2-O$, $P(=S)-O-CH=CCl_2$, $CH_3-NH$ (38) | | 100 | 100 | 95 | 50 | | | |
| $\text{C}_6\text{H}_{11}-CH_2-CH_2-CH_2-O$, $P(=S)-OCH=CCl_2$, $CH_3-NH$ (90) | | 100 | 100 | 100 | 75 | | | |
| sec.-$C_4H_9O$, $P(=S)-OCH=CCl_2$, $(CH_3)_2N$ (110) | | 100 | 100 | 100 | 100 | 75 | 50 | |
| $CH_3O$, $P(=O)-O-CH=CCl_2$, $CH_3O$ (known) (A) | | 0 | | | | | | |
| $CH_3(CH_2)_3-CH_2-O$, $P(=O)-O-CH=CCl_2$, $CH_3NH$ (known) (E) | | 0 | | | | | | |
| $C_2H_5O$, $P(=O)-OCH=CCl_2$, $(CH_3)_2CH-NH$ (known) (G) | | 100 | 95 | 50 | 0 | | | |
| $CH_3O$, $P(=O)-OCH=CCl_2$, $(CH_3)_2CH-NH$ (known) (H) | | 50 | 0 | | | | | |
| $C_2H_5O$, $P(=O)-OCH=CCl_2$, $(CH_3)_2N$ (known) (M) | | 0 | | | | | | |
| $CH_3-CH_2-CH_2-CH_2-O$, $P(=O)-O-CH=CCl_2$, $CH_3-NH$ (known) (P) | | 0 | | | | | | |
| $C_4H_9-O-CH_2-CH_2-O$, $P(=O)-OCH=CCl_2$, $CH_3NH$ (known) (T) | | 100 | 100 | 50 | 0 | | | |

Table 7-continued

| Active compound | | (Phorbia brassicae maggots in the soil) Degree of destruction in % for an active compound concentration of | | | | | | |
|---|---|---|---|---|---|---|---|---|
| | ppm | 20 | 10 | 5 | 2.5 | 1.25 | 0.625 | 0.3125 |
| $C_2H_5O-CH_2-CH_2-O$<br>$\phantom{xxxxxxx}\diagdown\overset{O}{\underset{\phantom{x}}{\|}}$<br>$\phantom{xxxxxxxxxxx}P-OCH=CCl_2$<br>$\phantom{xxxxx}\diagup$<br>$\phantom{xxx}CH_3-NH$<br>(known) $\phantom{xxxxxxxx}$ (Q) | | 100 | 90 | 0 | | | | |
| $C_3H_7-O-CH_2-CH_2-O$<br>$\phantom{xxxxxxx}\diagdown\overset{O}{\underset{\phantom{x}}{\|}}$<br>$\phantom{xxxxxxxxxxx}P-OCH=CCl_2$<br>$\phantom{xxxxx}\diagup$<br>$\phantom{xxx}CH_3NH$<br>(known) $\phantom{xxxxxxxx}$ (S) | | 95 | 50 | 0 | | | | |

EXAMPLE 11

Test with parasitizing fly larvae (*Lucilia cuprina*)

Solvent: 35 parts by weight ethyleneglycolmonomethyl ether.

Emulsifier: 33 parts by weight nonylphenolpolyglycol ether.

To produce a suitable preparation of active compound, 30 parts by weight of the active substance concerned is mixed with the stated amount of solvent which contains the above mentioned proportion of emulsifier, and the concentrate so obtained is diluted with water to the desired concentration.

About 20 fly larvae (*Lucilia cuprina*) are put into a test-tube which contains about 1 cc of horse musculature. 0.5 ml of the preparation of active compound are applied to this horseflesh. After 24 hours, the degree of destruction is determined as a percentage. 100% means that all, 0% that no, larvae have been killed.

The results obtained can be seen from the following Table 8:

Table 8

| Active compound | | Concentration of active compound in ppm | Degree of destruction in % (*Lucilia cuprina*) |
|---|---|---|---|
| $C_2H_5-O-\underset{NH-CH_3}{\overset{\overset{S}{\|}}{P}}-O-CH=CCl_2$ | (1) | 300<br>100<br>30<br>10<br>3<br>1 | 100<br>100<br>100<br>100<br>100<br><50 |
| $CH_3O-\underset{NH-CH(CH_3)_2}{\overset{\overset{S}{\|}}{P}}-O-CH=CCl_2$ | (8) | 300<br>100<br>30<br>10 | 100<br>100<br>100<br>100 |
| $CH_2=CH-CH_2-NH-\underset{}{\overset{\overset{H_3CO\ \ S}{\diagdown\ \|/}}{P}}-O-CH=CCl_2$ | (9) | 300<br>100<br>30<br>10 | 100<br>100<br>100<br>100 |
| $C_2H_5-O-\underset{NH-CH(CH_3)_2}{\overset{\overset{S}{\|}}{P}}-O-CH=CCl_2$ | (13) | 300<br>100<br>30<br>10 | 100<br>100<br>100<br>100 |
| $C_2H_5O-\underset{NH-CH_2-CH=CH_2}{\overset{\overset{S}{\|}}{P}}-O-CH=CCl_2$ | (14) | 300<br>100<br>30<br>10<br>3 | 100<br>100<br>100<br>100<br>100 |
| $(CH_3)_2CH-O-\underset{NH-CH_2-CH=CH_2}{\overset{\overset{S}{\|}}{P}}-O-CH=CCl_2$ | (36) | 300<br>100<br>30 | 100<br>100<br>100 |
| $\langle\phantom{x}\rangle-CH_2-CH_2-O-\underset{NH-CH_3}{\overset{\overset{S}{\|}}{P}}-O-CH=CCl_2$ | (97) | 300<br>100<br>30<br>10<br>3 | 100<br>100<br>100<br>100<br>100 |
| | | 300<br>100 | 100<br>100 |

Table 8-continued

| Active compound | | Concentration of active compound in ppm | Degree of destruction in % (Lucilia cuprina) |
|---|---|---|---|
| CH₃—CH₂—CH(CH₃)—O—P(=S)(O—CH=CCl₂)(NH—CH₃) | (42) | 30<br>10<br>3<br>1 | 100<br>100<br>100<br><50 |
| CH₃—CH₂—CH(CH₃)—O—P(=S)(O—CH=CCl₂)(NH—CH(CH₃)₂) | (43) | 300<br>100<br>30<br>10 | 100<br>100<br>100<br><50 |
| CH₃—CH₂—CH(CH₃)—O—P(=S)(O—CH=CCl₂)(NH—CH₂—CH=CH₂) | (44) | 300<br>100<br>30<br>10 | 100<br>100<br>100<br><50 |
| (CH₃)₂CH—CH₂—CH₂—O—P(=S)(O—CH=CCl₂)(NH—CH₃) | (47) | 300<br>100<br>30<br>10<br>3<br>1 | 100<br>100<br>100<br>100<br><50<br><50 |
| (CH₃)₂CH—CH₂—CH₂—O—P(=S)(O—CH=CCl₂)(NH—CH₂—CH=CH₂) | (50) | 300<br>100<br>30<br>10<br>3 | 100<br>100<br>100<br><50<br><50 |
| CH₃—(CH₂)₅—O—P(=S)(O—CH=CCl₂)(NH—CH₃) | (51) | 300<br>100<br>30<br>10<br>3 | 100<br>100<br>100<br>100<br>100 |
| CH₃—(CH₂)₅—O—P(=S)(O—CH=CCl₂)(NH—CH₂—C₆H₅) | (53) | 300<br>100<br>30<br>10 | 100<br>100<br>100<br>100 |
| CH₃—CH₂—CH(C₂H₅)—CH₂—O—P(=S)(O—CH=CCl₂)(NH—CH₃) | (54) | 300<br>100<br>30<br>10<br>3<br>1 | 100<br>100<br>100<br>100<br>100<br><50 |
| CH₃—CH₂—CH(C₂H₅)—CH₂—O—P(=S)(O—CH=CCl₂)(NH—CH₂—CH=CH₂) | (56) | 300<br>100<br>30<br>10 | 100<br>100<br>100<br><50 |
| CH₃—(CH₂)₆—O—P(=S)(O—CH=CCl₂)(NH—CH₃) | (57) | 300<br>100<br>30<br>10 | 100<br>100<br>100<br><50 |
| CH₃O—CH₂—CH₂—O—P(=S)(O—CH=CCl₂)(NH—CH(CH₃)₂) | (66) | 300<br>100<br>30<br>10<br>3 | 100<br>100<br>100<br><50<br><50 |
| C₆H₅—O—P(=S)(O—CH=CCl₂)(NH—CH₃) | (91) | 300<br>100<br>30<br>10<br>3<br>1 | 100<br>100<br>100<br>100<br>100<br><50 |
| C₆H₅—CH₂—CH₂—CH₂—O—P(=S)(O—CH=CCl₂)(NH—CH₃) | (101) | 300<br>100<br>30<br>10 | 100<br>100<br>100<br>100 |

Table 8-continued

| Active compound | | Concentration of active compound in ppm | Degree of destruction in % (Lucilia cuprina) |
|---|---|---|---|
| 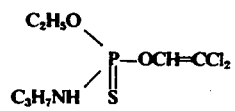 | (19) | 100<br>10<br>1 | 100<br>100<br>100 |
| 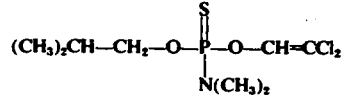 | (107) | 300<br>100<br>30<br>10 | 100<br>100<br>100<br>100 |
| 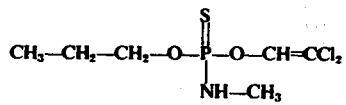 | (27) | 300<br>100<br>30<br>10 | 100<br>100<br>100<br>100 |
| 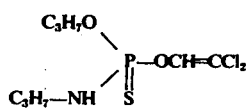 | (28) | 100<br>30<br>10<br>3<br>1 | 100<br>100<br>100<br>100<br>100 |
| 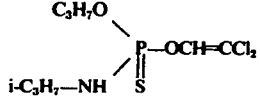 | (29) | 100<br>10<br>1 | 100<br>100<br><50 |
| 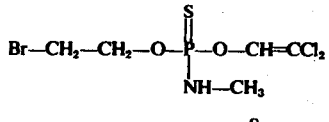 | (37) | 300<br>100<br>30<br>10<br>3 | 100<br>100<br>100<br>100<br><50 |
| 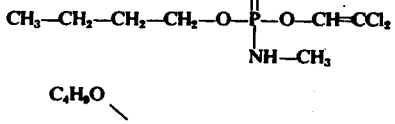 | (39) | 300<br>100<br>30<br>10<br>3 | 100<br>100<br>100<br>100<br>>50 |
| 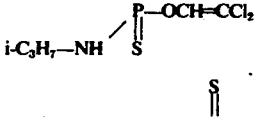 | (40) | 100<br>10 | 100<br>100 |
| 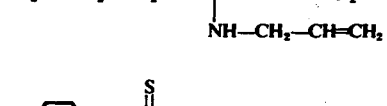 | (67) | 300<br>100<br>30<br>10<br>3 | 100<br>100<br>100<br><50<br><50 |
| 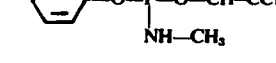 | (91) | 300<br>100<br>30<br>10<br>3 | 100<br>100<br>100<br>100<br>>50 |
| 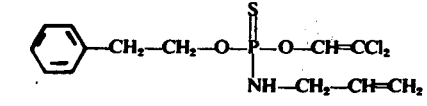 | (100) | 300<br>100<br>30<br>10 | 100<br>100<br>100<br><50 |
| 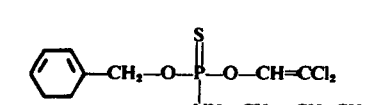 | (85) | 300<br>100<br>30<br>10 | 100<br>100<br>100<br>100 |
| 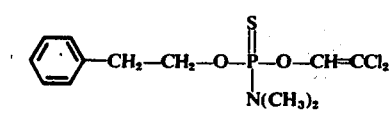 | (87) | 300<br>100<br>30 | 100<br>100<br>100 |

Table 8-continued

| Active compound | | Concentration of active compound in ppm | Degree of destruction in % (Lucilia cuprina) |
|---|---|---|---|
| $(CH_3)_2CH-CH_2-O-\underset{NH-CH_3}{\overset{\overset{S}{\|}}{P}}-O-CH=CCl_2$ | (45) | 300<br>100<br>30<br>10<br>3 | 100<br>100<br>100<br>100<br>>50 |
| $CH_3-CH_2-O-CH_2-CH_2-O-\underset{NH-CH_3}{\overset{\overset{S}{\|}}{P}}-O-CH=CCl_2$ | (68) | 300<br>100<br>30<br>10<br>3 | 100<br>100<br>100<br>100<br><50 |
| $CH_3-(CH_2)_3-O-CH_2-CH_2-O-\underset{NH-CH_3}{\overset{\overset{S}{\|}}{P}}-O-CH=CCl_2$ | (72) | 300<br>100<br>30<br>10<br>3 | 100<br>100<br>100<br>100<br>100 |

EXAMPLE 12

Tick test (*Boophilus microplus*)

Solvent: 35 parts by weight ethyleneglycolmonomethyl ether

Emulsifier: 35 parts by weight nonylphenolpolyglycol ether

To produce a suitable formulation, 3 parts by weight of the active compound are mixed with 7 parts by weight of the above-mentioned solvent-emulsifier mixture, and the emulsion concentrate so obtained is diluted with water to the concentration desired in each case.

Adult, gorged female ticks of the species *Boophilus microplus* (sensitive and resistant, respectively) are immersed for one minute in these preparations of the active compound. After immersion of, in each case, 10 female specimens of the various tick species, they are transferred to a Petri dish, the bottom of which is covered with a correspondingly large disc of filter paper.

After 10 days, the effectiveness of the preparation of active compound is determined by ascertaining the inhibition of egg deposition compared with untreated control ticks. The effect is expressed as a percentage, 100% meaning that eggs ceased to be deposited, and 0% signifying that the ticks deposited eggs in normal amount.

The active compounds investigated, the concentration tried, the parasites tested and the findings obtained can be seen from the following Table 9:

Table 9

| Active compound | | Concentration of active compound in ppm | Inhibition of egg deposition in % (Boophilus microplus Ridgeland strain) |
|---|---|---|---|
| $\text{C}_6\text{H}_5-CH_2-CH_2-O-\underset{NH-CH_3}{\overset{\overset{S}{\|}}{P}}-O-CH=CCl_2$ | (97) | 10 000<br>3 000<br>1 000<br>300<br>100<br>30 | 100<br>100<br>100<br>100<br>100<br><50 |
| $CH_3-CH_2-\underset{}{\overset{CH_3}{\underset{\|}{CH}}}-O-\underset{NH-CH_3}{\overset{\overset{S}{\|}}{P}}-O-CH=CCl_2$ | (42) | 10 000<br>3 000<br>1 000<br>300<br>100<br>30 | 100<br>100<br>100<br>100<br>>50<br><50 |
| $CH_3-CH_2-\underset{}{\overset{CH_3}{\underset{\|}{CH}}}-O-\underset{NH-CH(CH_3)_2}{\overset{\overset{S}{\|}}{P}}-O-CH=CCl_2$ | (43) | 10 000<br>3 000<br>1 000<br>300 | 100<br>100<br>100<br><50 |
| $CH_3-CH_2-\underset{}{\overset{CH_3}{\underset{\|}{CH}}}-O-\underset{NH-CH_2-CH=CH_2}{\overset{\overset{S}{\|}}{P}}-O-CH=CCl_2$ | (44) | 10 000<br>3 000<br>1 000<br>300<br>100<br>30 | 100<br>100<br>100<br>100<br>>50<br><50 |
| $(CH_3)_2CH-CH_2-CH_2-O-\underset{NH-CH_3}{\overset{\overset{S}{\|}}{P}}-O-CH=CCl_2$ | (47) | 10 000<br>3 000<br>1 000<br>300<br>100<br>30 | 100<br>100<br>100<br>100<br>100<br>100 |

Table 9-continued

| Active compound | | Concentration of active compound in ppm | Inhibition of egg deposition in % (Boophilus microplus Ridgeland strain) |
|---|---|---|---|
| $(CH_3)_2CH-CH_2-CH_2-O-\overset{\overset{S}{\|}}{P}(NH-CH_2-CH=CH_2)-O-CH=CCl_2$ | (50) | 10 000<br>3 000<br>1 000<br>300<br>100<br>30 | 100<br>100<br>100<br>>50<br><50<br><50 |
| $CH_3-(CH_2)_5-O-\overset{\overset{S}{\|}}{P}(NH-CH_3)-O-CH=CCl_2$ | (51) | 10 000<br>3 000<br>1 000<br>300<br>100 | 100<br>100<br>100<br>100<br><50 |
| $CH_3-(CH_2)_4-CH_2-O-\overset{\overset{S}{\|}}{P}(NH-CH_2-CH=CH_2)-O-CH=CCl_2$ | (52) | 10 000<br>3 000<br>1 000<br>300<br>100 | 100<br>100<br>100<br>>50<br>>50 |
| $CH_3-(CH_2)_5-O-\overset{\overset{S}{\|}}{P}(NH-CH_2-C_6H_5)-O-CH=CCl_2$ | (53) | 10 000<br>3 000<br>1 000<br>300 | 100<br>100<br>>50<br>>50 |
| $CH_3-CH_2-CH(C_2H_5)-CH_2-O-\overset{\overset{S}{\|}}{P}(NH-CH_3)-OCH=CCl_2$ | (54) | 10 000<br>3 000<br>1 000<br>300<br>100<br>30 | 100<br>100<br>100<br>100<br>100<br><50 |
| $CH_3-CH_2-CH(C_2H_5)-CH_2-O-\overset{\overset{S}{\|}}{P}(NH-CH(CH_3)_2)-O-CH=CCl_2$ | (55) | 10 000<br>3 000<br>1 000<br>300<br>100 | 100<br>100<br>100<br>>50<br><50 |
| $CH_3-CH_2-CH(C_2H_5)-CH_2-O-\overset{\overset{S}{\|}}{P}(NH-CH_2-CH=CH_2)-O-CH=CCl_2$ | (56) | 10 000<br>3 000<br>1 000<br>300<br>100<br>30 | 100<br>100<br>100<br>100<br>100<br>>50 |
| $CH_3-(CH_2)_8-O-\overset{\overset{S}{\|}}{P}(NH-CH_3)-O-CH=CCl_2$ | (57) | 10 000<br>3 000<br>1 000 | 100<br>100<br><50 |
| $C_6H_{11}-O-\overset{\overset{S}{\|}}{P}(NH-CH_2-CH=CH_2)-O-CH=CCl_2$ | (78) | 10 000<br>3 000<br>1 000<br>300<br>100<br>30 | 100<br>100<br>100<br>100<br>100<br>>50 |
| cyclopentyl-$O-\overset{\overset{S}{\|}}{P}(NH-CH_3)-O-CH=CCl_2$ | (73) | 10 000<br>1 000<br>100 | 100<br>100<br>>50 |
| cyclopentyl-$O-\overset{\overset{S}{\|}}{P}(NH-CH_2-CH=CH_2)-O-CH=CCl_2$ | (75) | 10 000<br>1 000<br>100 | 100<br>100<br>100 |
| cyclohexyl-$O-\overset{\overset{S}{\|}}{P}(NH-CH_3)-O-CH=CCl_2$ | (76) | 10 000<br>3 000<br>1 000<br>300<br>100<br>30 | 100<br>100<br>100<br>100<br>>50<br><50 |

Table 9-continued

| Active compound | Concentration of active compound in ppm | Inhibition of egg deposition in % (Boophilus microplus Ridgeland strain) |
|---|---|---|
| Ph-CH$_2$-CH$_2$-O-P(S)(OCH=CCl$_2$)-NH-CH$_2$-CH=CH$_2$ (100) | 10 000<br>3 000<br>1 000<br>300<br>100 | 100<br>100<br>100<br>100<br><50 |
| (cyclohexyl-H)-CH$_2$-O-P(S)(O-CH=CCl$_2$)-NH-CH$_2$-CH=CH$_2$ (82) | 10 000<br>3 000<br>1 000<br>300<br>100 | 100<br>100<br>100<br>100<br>100 |
| (cyclohexenyl)-CH$_2$-O-P(S)(O-CH=CCl$_2$)-NH-CH$_3$ (83) | 10 000<br>3 000<br>1 000<br>300<br>100<br>30 | 100<br>100<br>100<br>100<br>100<br>>50 |
| Ph-O-P(S)(O-CH=CCl$_2$)-NH-CH$_3$ (91) | 10 000<br>3 000<br>1 000<br>300<br>100 | 100<br>100<br>100<br>>50<br><50 |
| Ph-CH$_2$-CH$_2$-CH$_2$-O-P(S)(O-CH=CCl$_2$)-NH-CH$_3$ (101) | 10 000<br>3 000<br>1 000<br>300<br>100 | 100<br>100<br>100<br>100<br>>50 |
| CH$_3$-CH$_2$-CH$_2$-CH$_2$-O-P(S)(O-CH=CCl$_2$)-NH-CH$_3$ (39) | 10 000<br>3 000<br>1 000<br>300<br>100 | 100<br>100<br>100<br>>50<br>>50 |
| CH$_3$-(CH$_2$)$_3$-CH$_2$-O-P(S)(O-CH=CCl$_2$)-NH-CH$_3$ (46) | 10 000<br>3 000<br>1 000<br>300<br>100 | 100<br>100<br>100<br>100<br>100 |
| CH$_3$-CH$_2$-O-CH$_2$-CH$_2$-O-P(S)(O-CH=CCl$_2$)-NH-CH$_3$ (68) | 10 000<br>3 000<br>1 000<br>300<br>100<br>30 | 100<br>100<br>100<br>100<br>100<br>100 |
| CH$_3$-CH$_2$-CH$_2$-O-CH$_2$-CH$_2$-O-P(S)(O-CH=CCl$_2$)-NH-CH$_3$ (70) | 10 000<br>3 000<br>1 000<br>300<br>100<br>30 | 100<br>100<br>100<br>100<br>100<br>100 |
| CH$_3$-(CH$_2$)$_3$-O-CH$_2$-CH$_2$-O-P(S)(O-CH=CCl$_2$)-NH-CH$_3$ (72) | 10 000<br>3 000<br>1 000<br>300<br>100<br>30<br>10 | 100<br>100<br>100<br>100<br>100<br>100<br>100 |

EXAMPLE 13

Plutella test

Solvent: 3 parts by weight Acetone
Emulsifier: 1 part by weight Alkylaryl polyglycol ether To produce a suitable preparation of active compound, 1 part by weight of the active compound is mixed with the stated amount of solvent and the stated amount of emulsifier and the concentrate is diluted with water to the desired concentration.

Cabbage leaves (*Brassica oleracea*) are sprayed with the preparation of the active compound until dew moist and are then infested with caterpillars of the diamond-back moth (*Plutella maculipennis*).

After the specified periods of time, the degree of destruction is determined as a percentage; 100% means that all the caterpillars are killed whereas 0% means that none of the caterpillars are killed.

The active compounds, the concentrations of the active compounds, the evaluation times and the results can be seen from the following Table 10:

Table 10
(*Plutella* test)

| Active compound (constitution) | Concentration of active compound in % | Degree of Destruction in % after 3 days |
|---|---|---|
| 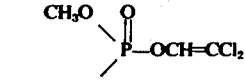 CH$_3$O\P—OCH=CCl$_2$ / C$_4$H$_9$—NH (known) (U) | 0.1<br>0.01<br>0.001 | 100<br>100<br>0 |
| CH$_3$O\P(S)—OCH=CCl$_2$ / C$_4$H$_9$—NH (10) | 0.1<br>0.01<br>0.001 | 100<br>100<br>100 |
| C$_2$H$_5$O\P(O)—OCH=CCl$_2$ / i-C$_3$H$_7$—NH (known) (G) | 0.1<br>0.01<br>0.001 | 100<br>100<br>0 |
| C$_2$H$_5$O\P(S)—OCH=CCl$_2$ / i-C$_3$H$_7$—NH (13) | 0.1<br>0.01<br>0.001 | 100<br>100<br>90 |
| C$_2$H$_5$O\P(O)—OCH=CCl$_2$ / C$_4$H$_9$—NH (known) (V) | 0.1<br>0.01<br>0.001 | 100<br>100<br>0 |
| C$_2$H$_5$O\P(S)—OCH=CCl$_2$ / C$_4$H$_9$—NH (15) | 0.1<br>0.01<br>0.001 | 100<br>100<br>80 |
| CH$_3$O\P(O)—O—CH=CCl$_2$ / C$_3$H$_7$—NH (known) (W) | 0.1<br>0.01<br>0.001 | 100<br>100<br>0 |
| CH$_3$O\P(O)—O—CH=CCl$_2$ / CH$_2$=CH—CH$_2$—NH (known) (K) | 0.1<br>0.01<br>0.001 | 100<br>100<br>0 |
| C$_4$H$_9$—O\P(S)—O—CH=CCl$_2$ / C$_4$H$_9$—NH (known) (D) | 0.1<br>0.01 | 100<br>0 |
| CH$_3$O\P(S)—O—CH=CCl$_2$ / C$_3$H$_7$—NH (7) | 0.1<br>0.01<br>0.001 | 100<br>100<br>85 |
| CH$_3$O\P(S)—O—CH=CCl$_2$ / CH$_2$=CH—CH$_2$—NH (9) | 0.1<br>0.01<br>0.001 | 100<br>100<br>100 |
| CH$_3$\ /CH—O\ P(S)—O—CH=CCl$_2$ C$_2$H$_5$/ / CH$_3$—NH (42) | 0.1<br>0.01<br>0.001 | 100<br>100<br>100 |

Table 10-continued

| Active compound (constitution) | (Plutella test) Concentration of active compound in % | Degree of Destruction in % after 3 days |
|---|---|---|
| $\begin{array}{c}CH_3\\CH_3\end{array}$CH—CH$_2$—O$\underset{C_2H_5-NH}{\diagdown}$P$\overset{S}{\overset{\|}{\diagdown}}$—O—CH=CCl$_2$  (116) | 0.01<br>0.001 | 100<br>90 |

EXAMPLE 14

Phaedon-Larvae-test

Solvent: 3 parts by weight Acetone
Emulsifier: 1 part by weight Alkylaryl polyglycol ether To produce a suitable preparation of the particular active compound, 1 part by weight of such active compound is mixed with the stated amount of solvent and the stated amount of emulsifier, and the resulting concentrate is diluted with water to the desired final concentration.

Cabbage leaves (Brassica oleracea) are sprayed with the preparation of the given active compound until dripping wet and then infested with the larvae of mustard beetles (Phaedon cochleariae).

After specified period of time, the degree of destruction is determined as a percentage: 100 % means that all the beetle larvae are killed, 0 % means that none of the beetle larvae are killed. The active compounds, the concentration used, the evaluation time and the results obtained can be seen from the following Table 11:

Table II

| Active compound (constitution) | (Phaedon Larvae Test) Concentration of active compound in % | Degree of Destruction in % after 3 days |
|---|---|---|
| $\begin{array}{c}CH_3O\\C_4H_9-NH\end{array}$P$\overset{O}{\overset{\|}{\diagdown}}$—OCH=CCl$_2$  (known)  (U) | 0.1<br>0.01<br>0.001 | 100<br>100<br>40 |
| $\begin{array}{c}CH_3O\\C_4H_9-NH\end{array}$P$\overset{S}{\overset{\|}{\diagdown}}$—OCH=CCl$_2$  (10) | 0.1<br>0.01<br>0.001<br>0.0001 | 100<br>100<br>100<br>30 |
| $\begin{array}{c}C_2H_5O\\CH_3-NH\end{array}$P$\overset{O}{\overset{\|}{\diagdown}}$—O—CH=CCl$_2$  (known)  (F) | 0.1<br>0.01<br>0.001 | 100<br>100<br>0 |
| $\begin{array}{c}C_2H_5O\\CH_3-NH\end{array}$P$\overset{S}{\overset{\|}{\diagdown}}$—OCH=CCl$_2$  (1) | 0.1<br>0.01<br>0.001 | 100<br>100<br>65 |
| $\begin{array}{c}C_6H_5-O\\CH_2=CH-CH_2-NH\end{array}$P$\overset{O}{\overset{\|}{\diagdown}}$—O—CH=CCl$_2$  (known)  (C) | 0.1<br>0.01 | 100<br>0 |
| $\begin{array}{c}C_6H_5-O\\CH_2=CH-CH_2-NH\end{array}$P$\overset{S}{\overset{\|}{\diagdown}}$—OCH=CCl$_2$  (93) | 0.1<br>0.01 | 100<br>70 |

EXAMPLE 15

Critical concentration-test/Soil insects

Test insect: *Phorbia antiqua*-Larvae in soil
Solvent: 3 parts by weight acetone
Emulsifier: 1 part by weight alkylarylpolyglycol ether To produce a suitable preparation of active compound 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance; only the amount by weight of active compound per unit volume of soil, which is given in p.p.m. (for example mg/l), is decisive. The soil is filled into pots and the pots are left to stand at room temperature. After 24 hours, the test animals are put into the treated soil and, after a further 48 hours, the degree of effectiveness of the active compound is determined as a percentage by counting the dead and living test insects. The degree of destruction is 100% when all the test insects have been killed; it is 0% when exactly as many test insects are still alive as in the case of the control.

The active compounds, the amounts applied and the results can be seen from the following Table 12.

Table 12

| Active Compound | *Phorbia antiqua* - Larvae in soil 2.5 ppm Active Material in Soil Effectiveness, % |
|---|---|
| C$_4$H$_9$—O\\P(=S)—O—CH=CCl$_2$ / C$_4$H$_9$—NH (known) (D) | 0 |
| CH$_3$\\ / CH—O\\P(=S)—OCH=CCl$_2$ / C$_2$H$_5$ / CH$_3$—NH (42) | 100 |
| CH$_3$O\\P(=S)—OCH=CCl$_2$ / CH$_2$=CH—CH$_2$—NH (9) | 100 |

Table 12-continued

| Active Compound | *Phorbia antiqua* - Larvae in soil 2.5 ppm Active Material in Soil Effectiveness, % |
|---|---|
| CH$_3$O\\P(=S)—OCH=CCl$_2$ / nC$_3$H$_7$—NH (7) | 100 |
| CH$_3$\\ / CH—O\\P(=S)—O—CH=CCl$_2$ / CH$_3$ / C$_2$H$_5$—NH (115) | 100 |
| CH$_3$\\ / CH—CH$_2$—O\\P(=S)—O—CH=CCl$_2$ / CH$_3$ / C$_2$H$_5$—NH (116) | 100 |

EXAMPLE 16

Doralis test (systemic action)

Solvent: 3 parts by weight acetone
Emulsifier: 1 part by weight alkylarylpolyglycol ether To produce a suitable preparation of active compound 1 part by weight of the active compound is mixed with the stated amount of solvent and the stated amount of emulsifier, and the concentrate is diluted with water to the desired concentration.

Bean plants (*Vicia faba*) which have been heavily infested with the bean aphid (*Doralis fabae*) are watered with the preparation of the active compound so that the preparation of active compound penetrates into the soil without wetting the leaves of the bean plants. The active compound is taken up by the bean plants from the soil and thus reaches the infested leaves.

After the specified period of time, the degree of destruction is determined as a percentage. 100% means that all the aphids are killed; 0% means that none of the aphids are killed.

The active compounds, the concentrations of the active compounds, the evaluation time and the results can be seen from the following Table 13.

Table 13

| | *Doralis* (Systemic) - Test Active Material Concentration in % | Degree of Destruction in % after 4 days |
|---|---|---|
| C$_4$H$_9$—O\\P(=S)—O—CH=CCl$_2$ / C$_4$H$_9$—NH (known) (D) | 0.1 | 0 |
| CH$_3$O\\P(=S)—O—CH=CCl$_2$ / C$_3$H$_7$—NH (7) | 0.1 | 100 |

Table 13-continued

| *Doralis* (Systemic) - Test | | |
|---|---|---|
| | Active Material Concentration in % | Degree of Destruction in % after 4 days |
| 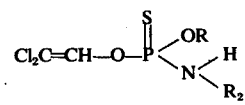 (42) | 0.1 | 100 |

It will be appreciated that the instant specification and examples are set forth by way of illustration and not limitation, and that various modifications and changes may be made without departing from the spirit and scope of the present invention.

What is claimed is:

1. A method of combating a pest slected from the group consisting of of insects, acarids and nematodes which comprises applying to such pest or its habitat an insecticidally, acaricidally or nematocidally effective amount of a dichlorovinylthionophosphoric acid ester amide of the formula

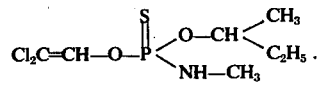

in which
R is methyl, isopropyl, isobutyl or sec.-butyl, and
R₂ is methyl, ethyl, propyl or allyl.

2. The method of claim 1, in which said compound is O-isobutyl-O-(2,2-dichlorovinyl)-N-methyl-thionophosphoric acid ester amide of the formula

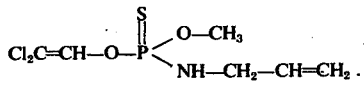

3. The method of claim 1, in which said compound is O-methyl-O-(2,2-dichlorovinyl)-N-allyl-thionophosphoric acid ester amide of the formula

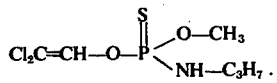

4. The method of claim 1, in which said compound is O-methyl-O-(2,2-dichlorovinyl)-N-propyl-thionophosphoric acid ester amide of the formula

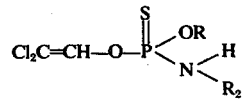

5. The method of claim 1, in which said compound is O-isopropyl-O-(2,2-dichlorovinyl)-N-ethyl-thionophosphoric acid ester amide of the formula

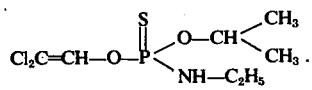

6. The method of claim 1, in which said compound is O-isobutyl-O-(2,2-dichlorovinyl)-N-ethyl-thionophosphoric acid ester amide of the formula

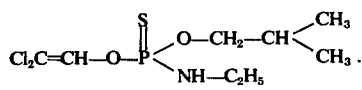

7. An insecticidal, acaricidal or nematocidal composition comprising an insecticidally, acaricidally or nematocidally effective amount of a dichlorovinylthionophosphoric acid ester amide of the formula in which
R is methyl, isopropyl, isobutyl or sec.-butyl, and
R₂ is methyl, ethyl, propyl or allyl
in admixture with a diluent.

8. A composition according to claim 7, wherein said ester amide is:
O-isobutyl-O-(2,2-dichlorovinyl)-N-methyl-thionophosphoric acid ester amide,
O-methyl-O-(2,2-dichlorovinyl)-N-allyl-thionophosphoric acid ester amide,
O-methyl-O-(2,2-dichlorovinyl)-N-propyl-thionophosphoric acid ester amide,
O-isopropyl-O-(2,2-dichlorovinyl)-N-ethyl-thionophosphoric acid ester amide, or
O-isobutyl-O-(2,2-dichlorovinyl)-N-ethyl-thionophosphoric acid ester amide.

* * * * *

UNITED STATES PATENT AND TRADEMARK OFFICE
CERTIFICATE OF CORRECTION

PATENT NO. : 4,013,795  
DATED : March 22, 1977  
INVENTOR(S) : Wilhelm Sirrenberg, et al Page 1 of 4

It is certified that error appears in the above-identified patent and that said Letters Patent are hereby corrected as shown below:

| | |
|---|---|
| Col. 2, line 63 | cancel "meaning" and substitute -- meanings -- |
| Col. 3, line 17 | after "phenethylamine" insert -- , -- |
| Col. 5, line 34 | cancel "kuhniella" and substitute -- kühniella -- |
| Col. 5, line 43 | cancel "A canthoscelides" and substitute -- Acanthoscelides -- |
| Col. 6, line 33 | cancel "pesticides" and substitute -- pesticide -- |
| Col. 6, lines 47-48 | cancel "Chlorobenzens" and substitute -- chlorobenzenes -- |
| Col. 9, line 32 | cancel "0.001" and substitute -- 0.01 -- |
| Col. 11, compounds 24, 25, 26 | formulas should be between columns $R_1$ and $R_2$ |
| Col. 15, compound 102 | cancel "$CH_2CH-CH_2$" and substitute -- $CH_2CH_2CH_2$ -- |

UNITED STATES PATENT AND TRADEMARK OFFICE
CERTIFICATE OF CORRECTION

PATENT NO. : 4,013,795
DATED : March 22, 1977
INVENTOR(S) : Wilhelm Sirrenberg et al It is certified that error appears in the above-identified patent and that said Letters Patent are hereby corrected as shown below:

Col. 17, compound 5     cancel
$$\begin{matrix} \text{"S} \\ \| \quad 0.1 \\ P-O- \quad \text{"} \end{matrix}$$
and substitute
$$\begin{matrix} -- \quad S \\ \| \\ P-O- \quad -- \end{matrix}$$

Col. 29, line 23     cancel "menatode" and substitute -- nematode --

Col. 30, line 23     cancel "with" and substitute -- into --

Col. 31, compound 72     cancel "90" and substitute -- 99 --

Col. 36, line 64     cancel "with" and substitute -- into --

Col. 40, compound 5     cancel "100" sixth occurrence and substitute -- 50 --

Col. 41, compound 110     unclear compound number should be -- $-C_4H_9O$ --

Col. 49, compound 4     unclear compound number should be -- $C_3H_7-O$ --

UNITED STATES PATENT AND TRADEMARK OFFICE
CERTIFICATE OF CORRECTION

PATENT NO. : 4,013,795

DATED : March 22, 1977

INVENTOR(S) : Wilhelm Sirrenberg et al

It is certified that error appears in the above—identified patent and that said Letters Patent is hereby corrected as shown below:

| | |
|---|---|
| Col. 49, compound 4 | cancel " $CH_3)_2N$ " and substitute -- $(CH_3)_2N$ -- |
| Col. 49, compound 111 | unclear compound number should be -- $C_4H_9\text{-}O$ -- |
| Col. 49, compound 111 | Cancel " $CH_3)_2N$ " and substitute -- $(CH_3)_2N$ -- |
| Col. 62, line 26 | delete "the" |
| Col. 62, compound 97 | move line to align "1000    100" in proper column |
| Col. 65, compound 83 | cancel "  " and substitute --  -- |

UNITED STATES PATENT AND TRADEMARK OFFICE
CERTIFICATE OF CORRECTION

PATENT NO. : 4,013,795

DATED : March 22, 1977

INVENTOR(S) : Wilhelm Sirrenberg et al

It is certified that error appears in the above—identified patent and that said Letters Patent is hereby corrected as shown below:

Col. 65, compound 39    move line to align "100    50" in proper column

Col. 65, compound 72    move line to align "10    100" in proper column

Signed and Sealed this

Twentieth Day of May 1980

[SEAL]

Attest:

SIDNEY A. DIAMOND

Attesting Officer      Commissioner of Patents and Trademarks